(12) United States Patent
Sonnenschein et al.

(10) Patent No.: US 7,344,493 B2
(45) Date of Patent: Mar. 18, 2008

(54) ENDOSCOPIC DEVICE HAVING ULTRASONIC POSITIONING

(75) Inventors: Elazar Sonnenschein, Beersheva (IL); Minelu Sonnenschein, Meitar (IL)

(73) Assignee: Medigus Ltd., Beer Sheva (IL)

( * ) Notice: Subject to any disclaimer, the term of this patent is extended or adjusted under 35 U.S.C. 154(b) by 1230 days.

(21) Appl. No.: 10/036,171

(22) Filed: Dec. 31, 2001

(65) Prior Publication Data
US 2002/0151767 A1    Oct. 17, 2002

(30) Foreign Application Priority Data
Feb. 26, 2001  (IL) .................................... 141665

(51) Int. Cl.
*A61B 1/01* (2006.01)
(52) U.S. Cl. ................... 600/117; 600/104; 600/145
(58) Field of Classification Search ............ 600/104, 600/106, 117, 118, 145, 130, 152
See application file for complete search history.

(56) References Cited

U.S. PATENT DOCUMENTS

| | | | |
|---|---|---|---|
| 4,805,453 A * | 2/1989 | Haynes ..................... 73/292 |
| 4,868,796 A * | 9/1989 | Ahrens et al. ............. 367/96 |
| 5,181,514 A | 1/1993 | Solomon et al. |
| 5,191,328 A | 3/1993 | Nelson |
| 5,259,837 A | 11/1993 | Van Wormer |
| 5,395,030 A * | 3/1995 | Kuramoto et al. ....... 227/179.1 |
| 5,445,144 A | 8/1995 | Wodicka et al. |
| 5,470,350 A | 11/1995 | Buchholtz et al. |
| 5,906,578 A | 5/1999 | Rajan et al. |
| 6,056,695 A | 5/2000 | Rupp et al. |
| 6,090,120 A | 7/2000 | Wright et al. |
| 6,149,598 A | 11/2000 | Tanaka |
| 6,159,146 A * | 12/2000 | El Gazayerli ............. 600/106 |
| 6,312,437 B1 * | 11/2001 | Kortenbach ............... 606/139 |
| 6,663,639 B1 * | 12/2003 | Laufer et al. ............. 606/139 |

(Continued)

FOREIGN PATENT DOCUMENTS

WO            9953838        10/1999

(Continued)

OTHER PUBLICATIONS

U.S. Appl. No. 10/030,018 entitled "Stapler for Endoscopes," filed Dec. 31, 2001, which claims priority to PCT/IL/01/00719, filed Aug. 2, 2001, claiming a priority date of Nov. 20, 2000.

(Continued)

*Primary Examiner*—John P. Leubecker
(74) *Attorney, Agent, or Firm*—Roach Brown McCarthy & Gruber, P.C.; Kevin D. McCarthy

(57) ABSTRACT

An endoscopic device includes ultrasonic emitters, receivers, and reflectors for the precise alignment of parts of an endoscope relative to each other. The methods for determining the relative position of two parts of the endoscope are based on measuring the distance between them based on the use of one or more transducers or arrays of transducers functioning as transmitters of ultrasonic signals and one or more transducers or arrays of transducers functioning as receivers of the ultrasonic signals. In preferred embodiments of the invention, at least one of the receivers is replaced by a reflector and at least one of the transmitters also functions as a receiver.

56 Claims, 25 Drawing Sheets

U.S. PATENT DOCUMENTS

| | | | | |
|---|---|---|---|---|
| 6,716,233 B1 | * | 4/2004 | Whitman | 606/219 |
| 6,872,214 B2 | * | 3/2005 | Sonnenschein et al. | 606/153 |
| 7,156,863 B2 | * | 1/2007 | Sonnenschein et al. | 606/219 |

FOREIGN PATENT DOCUMENTS

WO      WO 0239909      5/2002

OTHER PUBLICATIONS

U.S. Appl. No. 09/809,291 entitled "Fundoplication Apparatus and Method", filed Mar. 15, 2001, which claims priortiy to Israeli Application Nos. 135117 filed Mar. 16, 2001, 138632 filed Sep. 21, 2000, 139788 filed Nov. 20, 2000 and 141665 filed Feb. 26, 2001.

"Ultrasonic Bioinstrumentation", by Douglas A. Christensen, p. 131.

"Acoustic Waves: Devices, Imaging, and Analog Signal Processing" by Professor Gordon S. Kino, New Jersey: Prentice-Hall, Inc., 1987, pp. 175, 220-225.

"Digital Signal Processing, Principles, Algorithms, and Applications", by John G. Proakis, Third Edition, Prentice-Hall International Inc., New Jersey: 1966, pp. 30, 130-131.

"Acoustics, Schaum's Outline Series", by William W. Seto, McGraw-Hill Inc., USA, 1971, pp. 13-14.

"Ultrasonic Bioinstrumentation", by Douglas A. Christensen, 1998, p. 131.

* cited by examiner

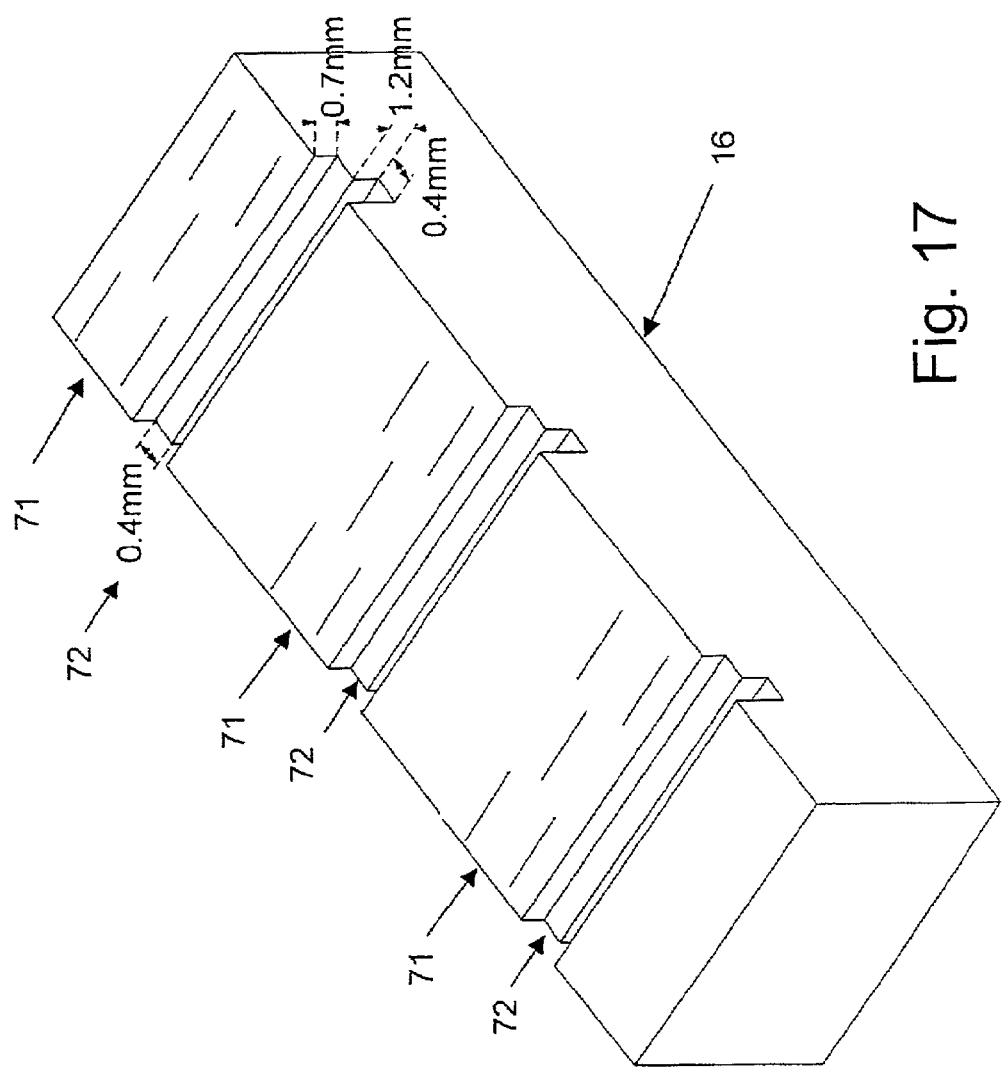

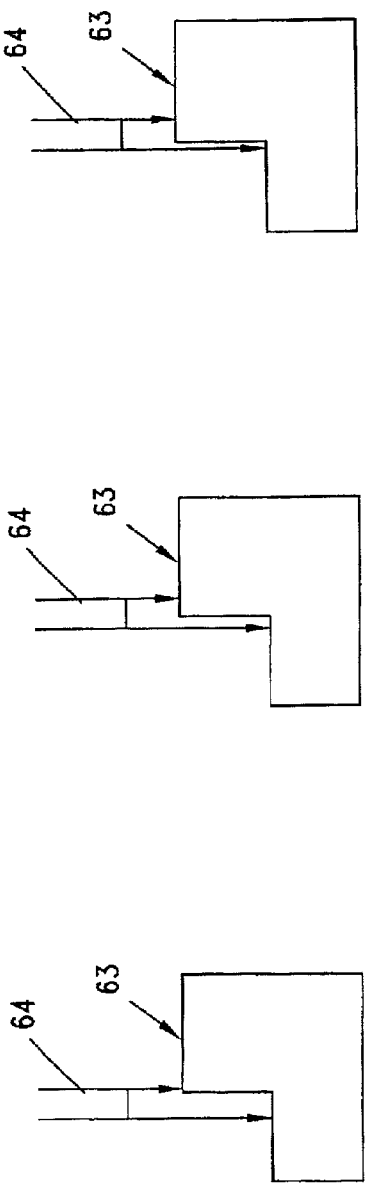
Fig. 25A
Fig. 25B
Fig. 25C
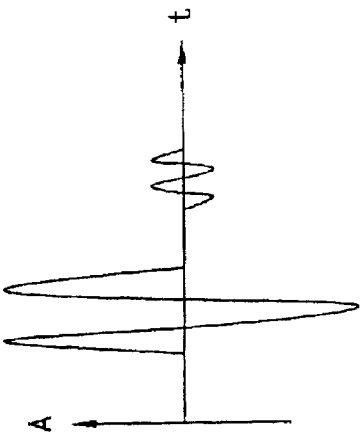
Fig. 25D
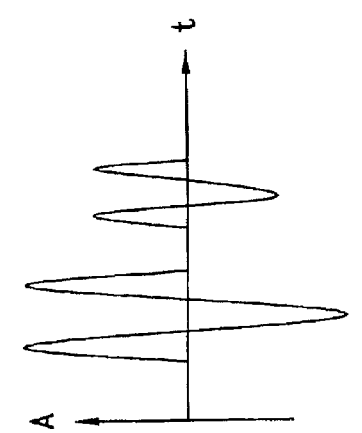
Fig. 25E
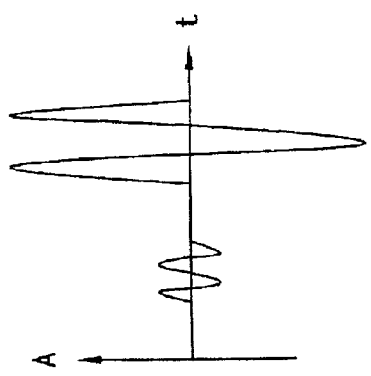
Fig. 25F

ENDOSCOPIC DEVICE HAVING ULTRASONIC POSITIONING

FIELD OF THE INVENTION

The present invention relates to the field of ultrasonic devices. More particularly the invention is related to the use of ultrasonic emitters, receivers, and reflectors for use in the positioning of different objects relative to each other. More specifically, the invention relates to the use of ultrasonic devices and techniques for the precise alignment of parts of an endoscope relative to each other.

BACKGROUND OF THE INVENTION

Many varied uses of ultrasound techniques in conjunction with non-invasive medical procedures involving catheters, laparoscopes, and endoscopes are known in the art. For example, U.S. Pat. No. 5,181,514, U.S. Pat. No. 5,259,837, U.S. Pat. No. 5,445,144, and U.S. Pat. No. 5,906,578 all disclose methods of using ultrasonic imaging to guide and position catheters or endoscopes within the human body. U.S. Pat. No. 6,149,598 discloses an ultrasound endoscope which combines the optical scan system of an endoscope with an ultrasound scanning system to monitor a surgical procedure, and U.S. Pat. No. 6,090,120 discloses an ultrasonic surgical instrument that can be used in endoscopic procedures.

In co-pending International Patent Applications PCT/IL01/00238 and PCT/IL01/00719 by the same applicant hereof, the descriptions of which are incorporated herein by reference, there is described an articulating endoscope containing a surgical stapler which consists of two parts, an anvil unit and a staple cartridge unit that are laterally distanced from each other along the axis of the endoscope. In the preferred embodiment of the invention, as disclosed in these applications, the staple cartridge unit is located in the shaft of the endoscope adjacent to the proximal end of the articulating section and the anvil unit is located in the distal tip of the endoscope at the distal end of the articulating section.

The movement of the distal tip relative to the cartridge is along a path that is a portion of a circle. It is imperative that the final stage of bending of the scope should end precisely at a certain location in order to actuate the stapling. Stopping at a location where the distance or alignment is not correct can cause faulty stapling and damage to the tissue. Therefore achieving proper distance and alignment of the distal tip relative to the cartridge, is indispensable to the proper functioning of the device.

A major technological problem that had to be addressed in the design and in the surgical application of this device is that of achieving and verifying the proper alignment and distance between the two parts of the stapler. As taught in the abovementioned patent applications, ultrasonic techniques known in the art can be used to accomplish the positioning. However, it has now been found that it is possible to improve the accuracy of the positioning of the endoscope, beyond that achievable by prior art techniques, which results in an important improvement in the reliability of operation.

It is therefore a purpose of this invention to provide methods for using ultrasound techniques to position separate parts of an endoscope with respect to each other, which improves over prior art methods.

It is another purpose of the present invention to provide devices that allow implementation of said methods for using ultrasound techniques to position separate parts of an endoscope with respect to each other.

It is a further purpose of the invention to provide procedures that assist in the implementation of said methods for using ultrasound techniques to position any elements, and in particular separate parts of an endoscope with respect to each other.

Further purposes and advantages of the invention will appear as the description proceeds.

SUMMARY OF THE INVENTION

In a first aspect the invention is directed to a method for determining the relative position of two objects comprising measuring the distance between the objects based on the use of one or more transducers or arrays of transducers functioning as transmitters of ultrasonic signals and one or more transducers or arrays of transducers functioning as receivers of the ultrasonic signals, and determining the degree of alignment therefrom. In some preferred embodiments of the invention, at least one of the transducers or arrays of transducers functioning as receivers of ultrasonic signals is replaced by a reflector and at least one of the transducers or arrays of transducers functioning as transmitters of the ultrasonic signals also functions as a receiver of the signals.

In some preferred embodiments of the invention, a single ultrasonic transducer, which is used to both transmit and receive the ultrasonic signals, is mounted on, or near, one object and at least one reflector is mounted on, or near, the second object. The reflector is suitable to reflect back a pattern that can be translated into the position and orientation of the objects relative to each other. In preferred embodiments of the invention, the reflector is comprised of two, or more, parallel reflecting planar surfaces forming one, or more, step-like configurations having rectangular or cylindrical symmetry.

The invention is also directed to a method of measuring the distance between two objects consisting of the following steps:
- generating a repetitive series of short electrical pulses or bursts of electrical pulses;
- amplifying the pulses;
- applying the amplified electric pulses to a transducer which converts the electrical energy to ultrasonic energy;
- allowing the ultrasonic energy to propagate, in the form of a relatively narrow beam, through a medium, until it encounters either another transducer or a reflector which directs it back towards the transducer from which it was emitted;
- receiving the ultrasonic energy by the transducer which converts it to an electrical signal;
- amplifying and filtering the electrical signal;
- digitizing the signal;
- temporarily storing the stored data in a separate buffer of a first-in first-out (FIFO) buffer or fast memory;
- transferring the data from the FIFO or fast memory into the main computer memory;
- correlating the data in each buffer with a predefined reference signal pattern stored in a computer memory;
- determining the time of flight of the ultrasonic signal from the index of the buffer where the correlation with the reference signal has its maximum value; and,
- determining the distance from the time of flight.

The invention is also directed to a method of determining the alignment of two parts relative to each other, comprising the following steps:

using a single transducer as the transmitter/receiver of the ultrasonic beam and a reflector having at least one-step, which will give at least two distinct signals in the return beam;

correlating the signals stored in the computer main memory with those of the predefined reference signal in the computer memory;

determining the step depths from the buffers corresponding to the maxima of the correlations, wherein, at least two local maxima of the correlation must exist and the difference(s) between them must correspond to the known depth(s) of the step(s);

if the measured depth(s) of the step(s) does not agree with the known depth(s) of the step(s), then moving the transducer relative to the reflector and carrying out the correlation again; and when the measured depth(s) of the step(s) does agree with the known depth(s) of the step(s), then using the energy amplitudes from the correlation buffer to determine the energy relation between the echoes in order to determine alignment or direction for displacement.

The invention is further directed to a method of determining and changing the displacement of two objects relative to each other comprising the following steps:

a) using a single transducer as the transmitter/receiver of the ultrasonic beam and a reflector having at least two-steps of different depths, which will give at least three distinct echoes in the return beam;

b) determining that the objects are not aligned if less than the expected number of echoes is returned;

c) determining the depth of the steps from the returned echoes;

d) comparing the measured depth with the known depths of the reflector, to determine the portion of the reflector upon which the ultrasonic beam impinges;

e) checking that the ratio of energy of the two echoes that match the step depths are within a certain relation;

f) using the information obtained in steps (d) and (e), to move the transmitter relative to the reflector; and g) repeating steps (b) to (f) until the transmitter is positioned directly in front of the reflector.

In a second aspect, the invention is directed to a reflector of ultrasonic waves that is suitable to reflect back a pattern that can be translated into the position and orientation of two objects relative to each other. The reflector of ultrasonic energy is comprised of two, or more, parallel reflecting planar surfaces forming one, or more, step-like configurations having rectangular or cylindrical symmetry.

In another aspect, the invention is directed to an endoscopic device comprising a system for measuring the distance between and/or the relative alignment of, two objects located at two different locations along the length of the endoscope. The system comprises one or more transducers or arrays of transducers functioning as transmitters of ultrasonic signals located on, or near, one of the objects, and one or more transducers or arrays of transducers functioning as receivers of ultrasonic signals located on, or near, the other of the objects. In a preferred embodiment of the endoscopic device of the invention, at least one of the transducers or arrays of transducers functioning as receivers of ultrasonic signals is replaced by a reflector and at least one of the transducers or arrays of transducers functioning as transmitters of the ultrasonic signals also functions as a receiver of the signals.

In some preferred embodiments of the endoscopic device of the invention, a single ultrasonic transducer, which is used to both transmit and receive the ultrasonic signals, is mounted on, or near, one of the objects and at least one reflector is mounted on, or near, the second object. The reflector is suitable to reflect back a pattern that can be translated into the position and orientation of the objects relative to each other. In a preferred embodiment of the invention, the reflector is comprised of two, or more, parallel reflecting planar surfaces forming one, or more, step-like configurations having rectangular or cylindrical symmetry.

In yet another aspect, the invention is directed to endoscopic device wherein an anvil unit of a stapler system is one of the objects to be aligned, and a stapler deployment unit containing a stapler cartridge is the other object.

In a further aspect, the invention is directed to a stapler cartridge containing one or more reflectors of ultrasonic energy that are created as an integral part of the cartridge, on or within its surface.

In a preferred embodiment of the invention, the stapler cartridge contains one or more channels created throughout its height for guiding an ultrasonic signal from a transmitter, located on one side of the cartridge, to a receiver of the signal, located on the other side.

All the above and other characteristics and advantages of the invention will be further understood through the following illustrative and non-limitative description of preferred embodiments thereof, with reference to the appended drawings.

BRIEF DESCRIPTION OF THE DRAWINGS

FIG. 17 schematically shows two-step reflectors on a staple cartridge;

FIGS. 25A-25F schematically illustrate the alignment procedure.

DETAILED DESCRIPTION OF THE PREFERRED EMBODIMENTS

Figure 1:
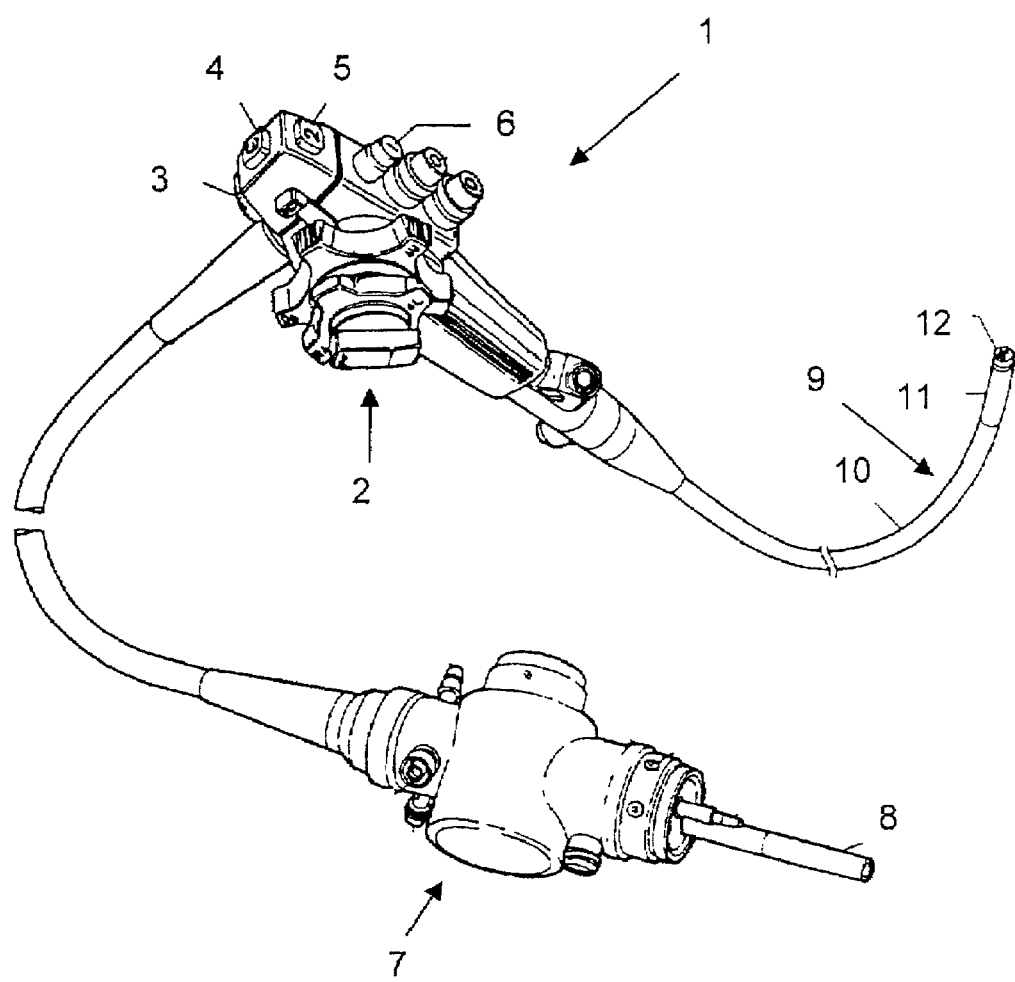
FIG. 1 schematically illustrates a conventional endoscope

The invention will now be explained through the illustrative and non-limitative description of preferred embodiments. A conventional endoscope is illustrated in FIG. 1. This endoscope comprises several features, such as the operating switches, the angulation lock, etc., that may be present in the device of the invention, but that will not be described in detail in the description to follow, because they are conventional and well known to the skilled person. Thus, in the following description only elements needed to illustrate the invention will be described. Briefly, however, the endoscope illustrated in FIG. 1 and generally indicated at 1, is provided with a control section 2 provided with suction valves, locks, switches, etc., switches 3-6 being marked for illustration purposes. It also comprises a connector section 7, used to connect air and water inlets, light guides, electrical conductors for ultrasound signals, etc. The conductors for ultrasound signals being indicated at 8, for illustration purposes. The insertion tube 9 consists of three separate sections: a flexible portion 10, an articulation section 11 and a distal end 12. The articulation section is shown in greater detail in FIG. 2, which also shows the distal tip 13 in which the distal end 12 resides.

Figure 2:
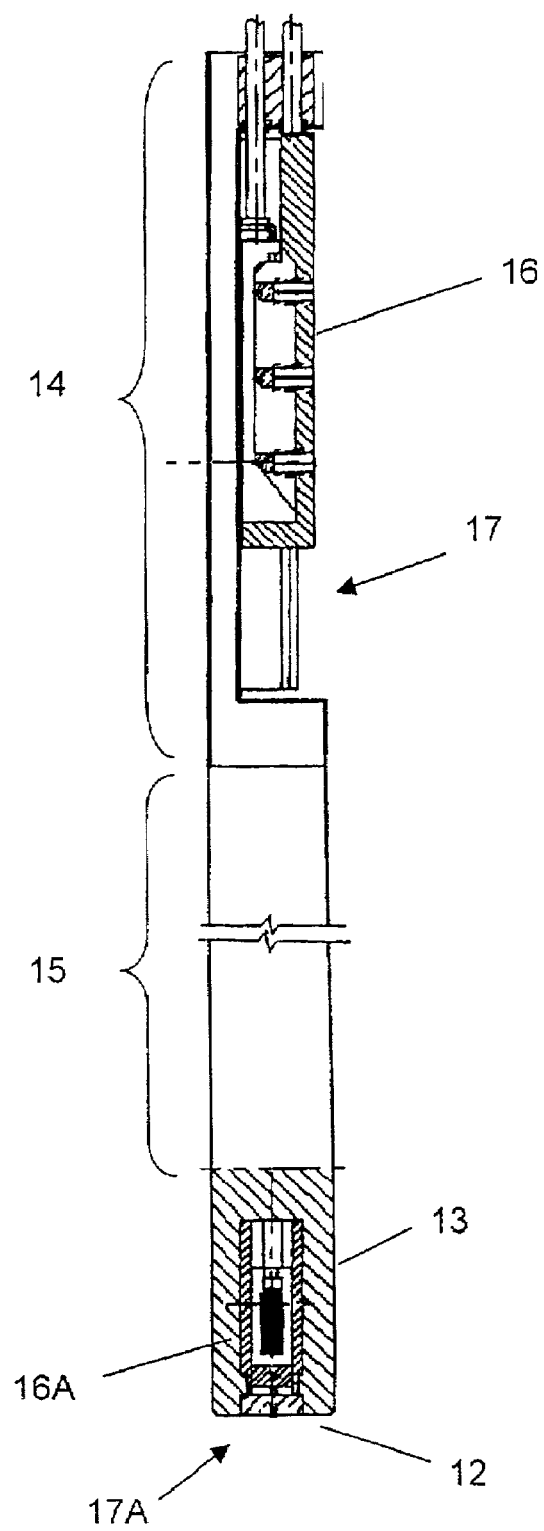
FIG. 2 schematically illustrates the fixed portion and the articulation distal portion of an endoscope, comprising a surgical stapler according to a preferred embodiment of the invention.

Looking now at FIG. 2, the distal portion of an endoscope, according to a preferred embodiment of the invention of International Patent Application PCT/IL01/0719 is schematically shown. This portion comprises a staple firing mechanism indicated at 14, and an articulating section 15, and the distal tip 13. The section 11 of FIG. 1 is composed of sections 13 and 15.

Articulating section 15 is similar in design to that of conventional endoscopes, but possesses several unique features. In order to simplify the alignment procedure and at the same time achieve maximum accuracy, a two-way articulation design was chosen for the illustrative preferred embodiment of the invention of the above referenced application. This means that the articulating section is constrained to bend in one direction only (i.e. the tip of the endoscope can only bend from straight ahead to one side and back to a relatively fixed plane). Secondly, the device is able to bend up to 270° in order to carry out the required medical procedure, which is further than in conventional endoscopes. Finally, the articulating section is strong enough to provide a significant force against the tissues during the surgical operation.

In another embodiment of the invention, a four-way articulation system is employed. In a four-way system the tip of the endoscope can be moved in two mutually perpendicular planes. This gives more degrees of freedom of movement, but complicates the alignment procedure and necessitates the use of one of the alignment systems to be described below. Four-way systems are well known in the art and therefore will not be described here for the sake of brevity.

According to a preferred embodiment of PCT/IL01/00719, the stapler cartridge is positioned at the proximal end of the articulation section, 15. The stapler deployment system has a side firing design and requires an anvil, which is located on the end of the distal tip. Both the stapler cartridge 16 and the anvil module 16A are replaceable and fit into receptacles on the shaft and distal tip. These receptacles are labeled 17 and 17A respectively in FIG. 2. The stapling elements 16 and 16A, together, form the entire stapling assembly.

Figure 3:
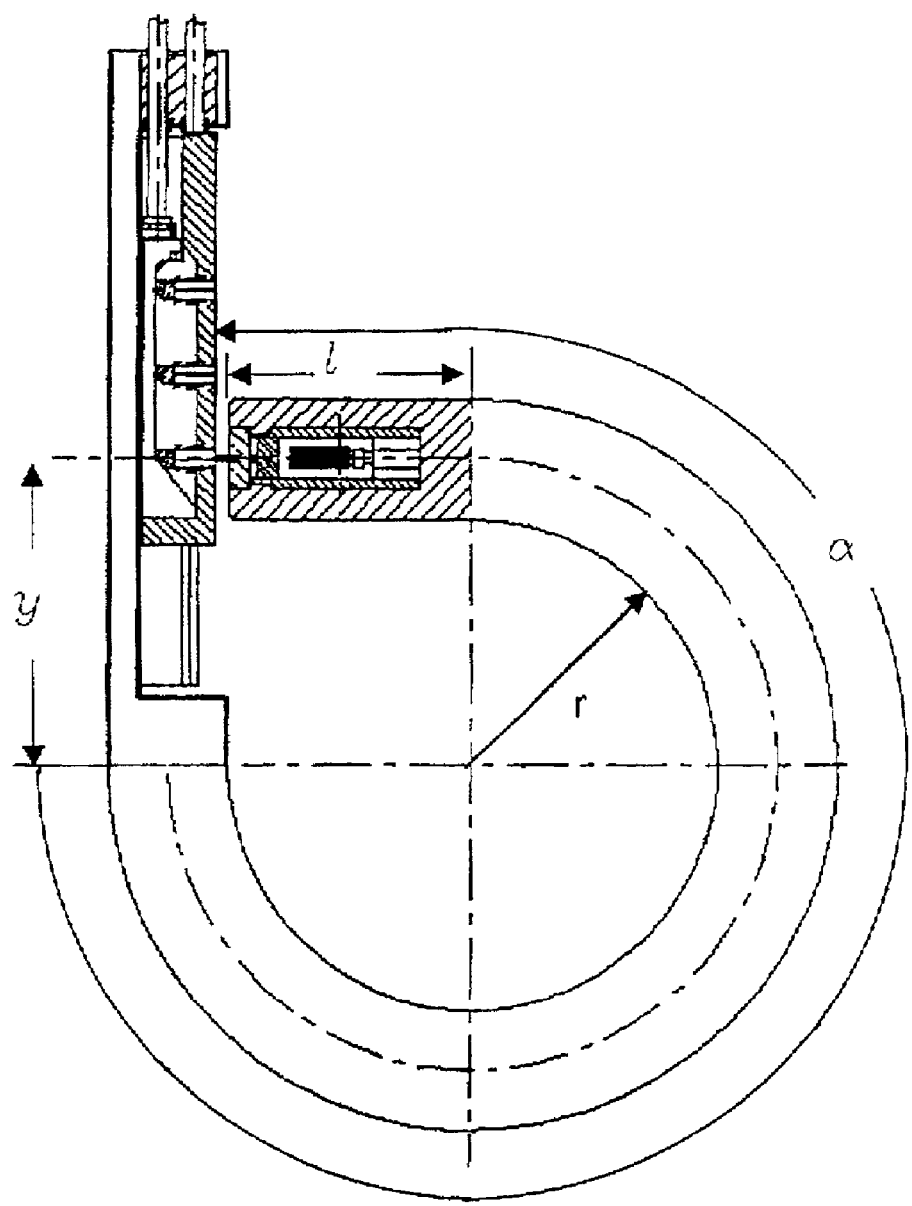
FIG. 3 schematically illustrates the articulation of the endoscope of FIG. 2 through its maximum bending angle.

FIG. 3 schematically shows the device of FIG. 2 in a fully articulated position. The articulation section 15 has been bent through bending angle α using fixed radius of curvature "r". The values of radius "r" and the length of the articulation section are determined by the fixed values "l" (length of the rigid distal tip) and "y" (the distance from the position at which the stapling is to be carried out to the proximal end of the articulation portion of the endoscope) in such a way that articulation of the device completely brings the two parts of the stapler assembly exactly into alignment. However, alignment detection is still needed to insure proper functioning, e.g., when freedom of movement exists in the joints of the articulation section, due to wear.

Figure 4:
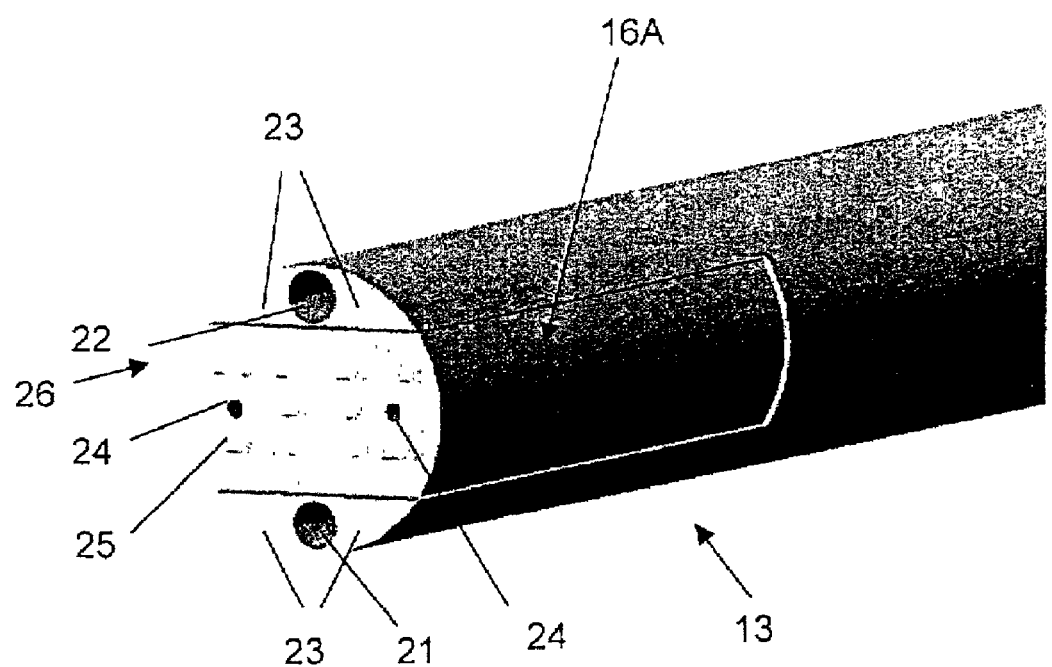
FIG. 4 shows the distal tip of the endoscope of FIG. 2, with the anvil module of the stapler assembly in place.

FIG. 4 schematically shows the distal tip of the endoscope (section 13 in FIG. 2) with the anvil unit 16A in place. A channel for suction, irrigation, or any other purpose is shown at 21. The imaging channel is designated by numeral 22 and numeral 23 designates illumination fibers. Numeral 24 designates the holes through which the alignment/locking pins exit the anvil unit. Numeral 25 designates the depressions for curling the staples on the anvil unit face (generally designated by the numeral 26). The function and method of operation of these parts is not relevant to the present invention and therefore will not be discussed here.

The skilled person will understand that other options can be provided and other configurations are allowed depending on the requirements of the endoscopic procedure to be performed. As one example, a transducer, receiver, or reflector can be placed at one of positions 23 or 26, for use in ultrasound positioning as described below.

Figure 5:
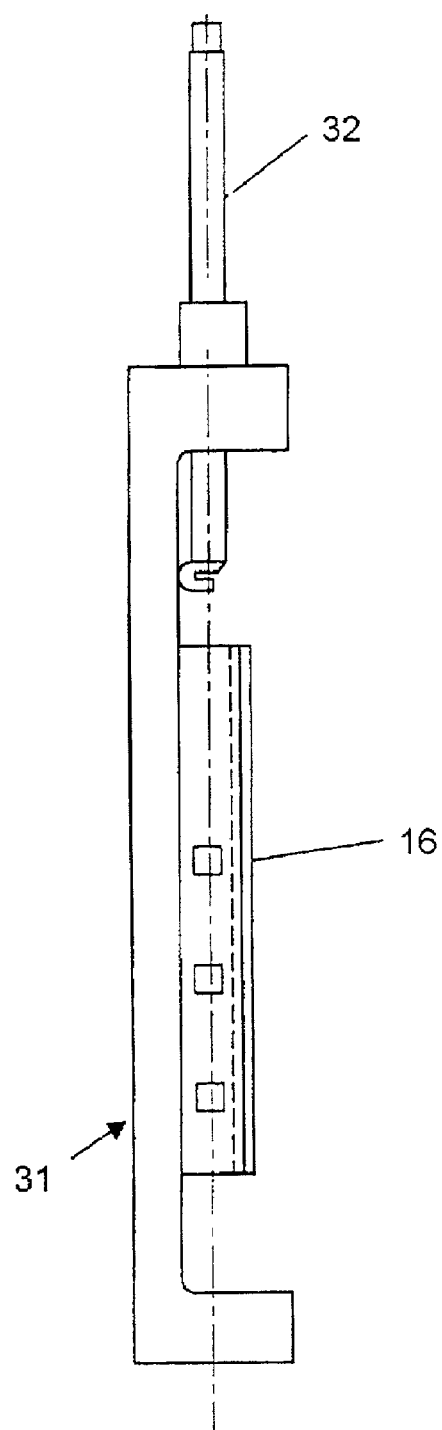
FIG. 5 schematically shows the side view of the staple cartridge holder in the shaft of the endoscope of FIG. 2.

The second part of the stapler consists of a staple cartridge holder with disposable stapler cartridge located in the fixed portion of the endoscope shaft, proximate to the articulation section. FIG. 5 is a side view that schematically shows those parts that are located at 17 in FIG. 2. The staple cartridge holder 31 consists of a tube of appropriate inside and outside diameters with a cutout in the profile. Within, the cutout is fitted with a piece of formed sheet metal (not shown) that forms a hermetic seal and retains the disposable staple cartridge 16 in the appropriate location with accurate index locations for the transfer of the staple cartridge for subsequent firings.

Attached to the tube and sheet metal subassembly is a plunger guide complete with a seal fitted with a plunger (collectively designated by the numeral 32). The plunger fires an array of staples when pulled in a proximal direction and then indexes the staple cartridge to the next position by a push motion in the distal direction.

The disposable cartridge case contains two subassemblies, a cartridge body and an activation cam subassembly. (As in the case of the anvil assembly, a detailed description of these two subassemblies is given in the above referenced patent applications and will not be repeated here since it is not needed to describe and to understand the present invention.)

It is also understood by the man of the art that the positions of the stapler deployment system and the anvil can be interchanged and that the elements of the stapler can be located at different positions along the long axis of the endoscope. For example, one part of the stapler system can be located proximally from the connection between the articulation and flexible sections within the flexible shaft of the endoscope. It is even possible, in certain cases, to reduce the radius of curvature of the device by placing the staple cartridge on one of the links of the articulation section, for example, if only one array of staples is to be fired.

The navigation and the positioning of the distal tip in front of the cartridge require two types of information:
1. Distance measurement (3-4 mm between the distal tip and the cartridge).
2. Alignment (defined here as the position and orientation of the object in some coordinate frame, i.e., three translations and three rotations; the desired tolerance is 0.5 mm).

Distance measurements are carried out most simply by various methods that are based on measurement the time of flight. These methods assume that the mean average velocity of an ultrasound wave propagating in a tissue has a constant value, for example 1500 m/s. By making this assumption, it is possible to estimate the distance by measuring the time of flight. There are basically two approaches that are used and they will be described with respect to the preferred embodiment of the endoscope described above.

In the first preferred embodiment of the invention employing a time of flight method, a single transducer is used for transmitting the ultrasound signal and receiving the echo that returns from a reflector. The distance is then calculated by measuring the time of a round trip, i.e. the time of a pulse that is emitted by the transducer (mounted, for example, on the cartridge), penetrates the tissue, is reflected back by the anvil, passes through the tissue again, and is received by the transducer. In this case the distance between the transducer and the reflector, d, is found from $$d = \frac{v_c \times t}{2}$$

Where, $v_c$ is the sound velocity (Approximately 1500 m/s) and the deviation by 2 denotes the fact that the pulse actually propagates twice the measured distance. In order to accomplish high resolutions, this method requires using very short pulses at high frequencies.

Another preferred embodiment of the invention, employing a time of flight method, makes use of two transducers. One is mounted on the distal tip and the other on the stapler cartridge. In this case the distance is calculated from, $$d = v_c \times t$$

The time of flight is measured by several different methods. The first and simplest preferred embodiment of the invention is based on energy detection. According to this method a clock is started simultaneously with the start of transmission and stopped when the energy input from the returning signal rises above a predefined threshold.

In another preferred embodiment of the invention, the time of flight is measured by transmitting a pulse and sampling the received signal in order to carry out a cross-correlation with a reference signal that is stored inside the computer memory. The cross-correlation method is more accurate than directly measuring the time of flight by the use of the threshold method. This is because the cross-correlation method compares the shapes of the received signal and is independent of the amplitude of the signals. The amplitude is constantly varying as a result of distortions caused by the electrical system and the medium through which the signal is propagated. Further, the cross-correlation method is based on integration of the signal, thus high-speed noise is filtered out and good results can be obtained even when the return signal is very weak.

The accuracy of the measurements in the second method can be improved by transmitting a random sequence of pulses, instead of a single pulse, and performing a correlation between the received sequence and a stored reference sequence. By modulating the random sequence with a digital modulation such as the well-known pulse shifted keyed (PSK) modulation, the reliability can be even further improved. Modulating a random sequence of pulses will help in detecting a weak signal that is immersed in noise. Further this type of correlation will reduce the measurement uncertainties that result from multipath and depth echoes.

In both methods, the velocity that is used is only an approximation and the resolution of the measurement is determined by the properties of the counter or the sampling rate clock that is employed.

The above methods of the time of flight measurements present some practical drawbacks. On the one hand, using only one transducer limits the minimal possible measuring distance to the length of the transmitted pulse; therefore, it is necessary to use very short pulses, which results in reduced accuracy. Also, the use of high frequencies will cause large attenuation of the propagating signal. On the other hand, use of the system that relies on two-transducers requires more space and increases the cost of the system.

Figure 6:
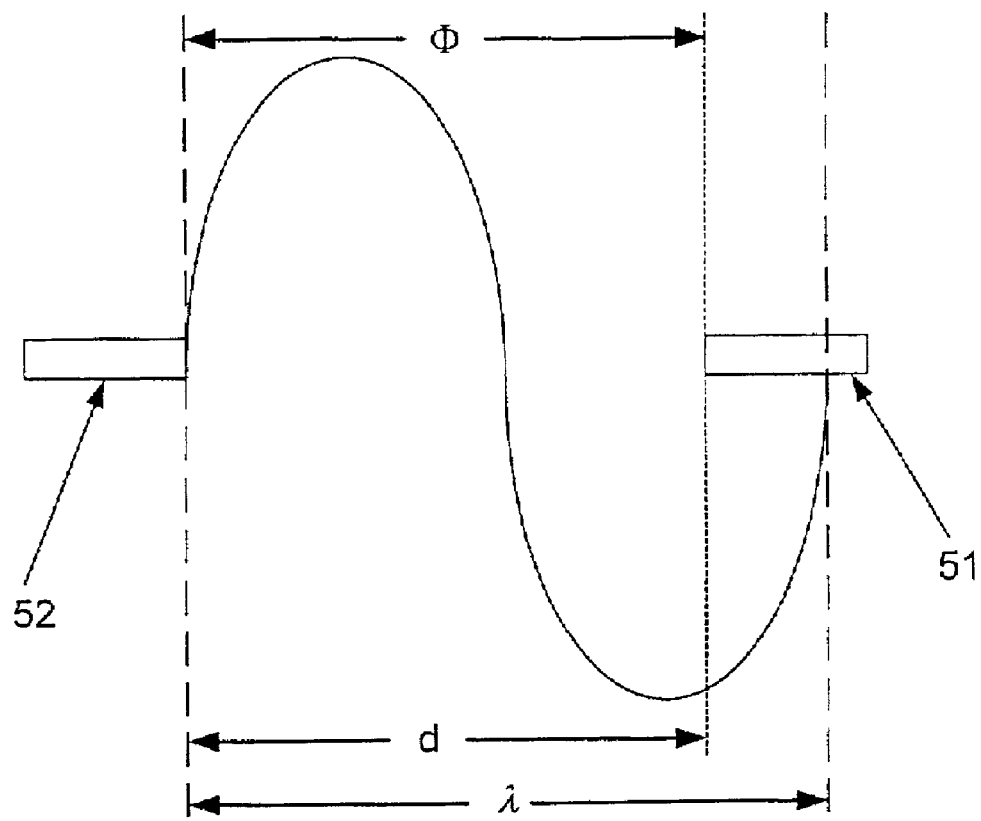
FIG. 6 schematically illustrates the spatial phase difference of measuring distance.

Another method for measuring the required distances is employed to overcome some of the abovementioned difficulties of the time of flight measurements. In this preferred embodiment of the invention, the spatial phase difference between the transmitted and the received wave is measured. FIG. 6 illustrates the method. If the measured phase angle is $\Phi$ and the wave length of the ultrasound signal is $\lambda$, and the distance between the transmitting transducer (numeral 52) and the receiver (numeral 51) is d, then:

$$d = \lambda \cdot \Phi / 360$$

As can be seen from FIG. 6, $A(d) = A_0 \sin(\Phi)$, where $A(d)$ is the measured signal and $A_0$ is a known value determined from a previous calibration measurement. Thus $\Phi$ can be calculated from the arcsine function and the distance is therefore determined from $$d = \frac{\lambda \cdot \arcsin\left(\frac{A(d)}{A_0}\right)}{360}$$

Since the arcsine function leads to two possible solutions for the distance, it is necessary to make at least two measurements from two adjacent spatial points in order to determine the direction of the slope and therefore the correct solution of the equation.

This method is restricted to low frequencies only; because the measuring distance is limited to only one wavelength (ambiguity will occur when the distance is greater than a single wavelength). In order to measure distance of 4-20 mm, for example, dictates working at frequencies in the range of 75-375 kHz.

The advantages of this method are that the precision is rather high in comparison with the time of flight method (since it is possible to extrapolate the distance from any measurement) and using low frequencies decreases the attenuation of the propagating signal. However, this method also assumes that all the tissue in the propagating path is the same. In addition, it is necessary to use at least two transducers; therefore the cost and space requirements are increased.

In another preferred embodiment of the invention, the time of flight and spatial phase difference methods are both used by commencing measurement from a relatively far distance by using the former method, and then when the distance is equal to or less than one wavelength, to begin measuring the phase difference. In order to use this approach for the purposes of the present invention, it is necessary to use an efficient transducer with a short diameter, such as 1-2 mm, that is capable of supporting two different frequencies, e.g., 150 kHz and 2 MHz.

The complexity of manufacturing a transducer with two different frequencies that are very far one from the other is overcome by measuring the acoustical transmission at two wavelengths, as follows: The received signal, $S_1$, derived from the acoustic signal of the transducer aperture is:

$$S_1 = R_1 \cdot A \cdot I_{t1} = R_1 \cdot A \cdot I_{01} \cdot e^{-a_1 \cdot z}$$

where, index 1 refers to wavelength 1, R is the transducer responsivity, A is area of the "illuminated" aperture that is seen by the transducer aperture, $I_t$ is the acoustic intensity that has traversed the medium, $I_0$ is the intensity that is radiated by the transmitting transducer, a is the absorption parameter, and Z is the distance that the beam travels through the absorbing medium. The second wavelength yields a similar equation, with index 2 replacing the index 1. The distance Z can be extracted from the quotient $S_1/S_2$ $$Z = \frac{1}{a_1 - a_2} \ln\left(\frac{R_1}{R_2}\right) \times \frac{I_{01}}{I_{02}} \bigg/ \frac{S_1}{S_2}$$

In the last expression, the term $(I_{01}/I_{02})$ is unknown, but could be recovered from a calibration measurement. The calibration measurement is a replica of the actual measurement; however the medium between the apertures has known absorption e.g., water. Denoting the signals from the absorption-free medium by $S_1'$ and $S_2'$ $$\frac{S_1'}{S_2'} = \frac{R_1}{R_2} \cdot \frac{I_{01}}{I_{02}}$$

hence, $$Z = \frac{1}{a_1 - a_2} \ln\left[\frac{S_1'}{S_2'} \bigg/ \frac{S_1}{S_2}\right].$$

As opposed to the phase measurement method, it is necessary to use only one transducer for both transmitting and receiving. In addition, although it is necessary to use a dual frequency transducer in both methods, in the last method described above, the difference between frequencies used does not have to be as great as in the phase measurement, making it easier and less costly to produce the transducer.

As in the case of the distance measurements, several methods can be proposed to enable the alignment of the endoscope. The simplest embodiment of the invention uses imaging by phase array to accomplish the distance measurements and alignment. Many small transducers comprise the array that is used for imaging as in the prior art. A conventional catheter transducer can be mounted on the distal tip and used to image the cartridge to carry out the alignment and distance measurements. Although this method is in principle based on existing techniques and easy to implement, the size of the transducer and accompanying electrical wires, as well as the cost, prevent this from being an embodiment of the invention that is preferred for most applications.

Figure 7:
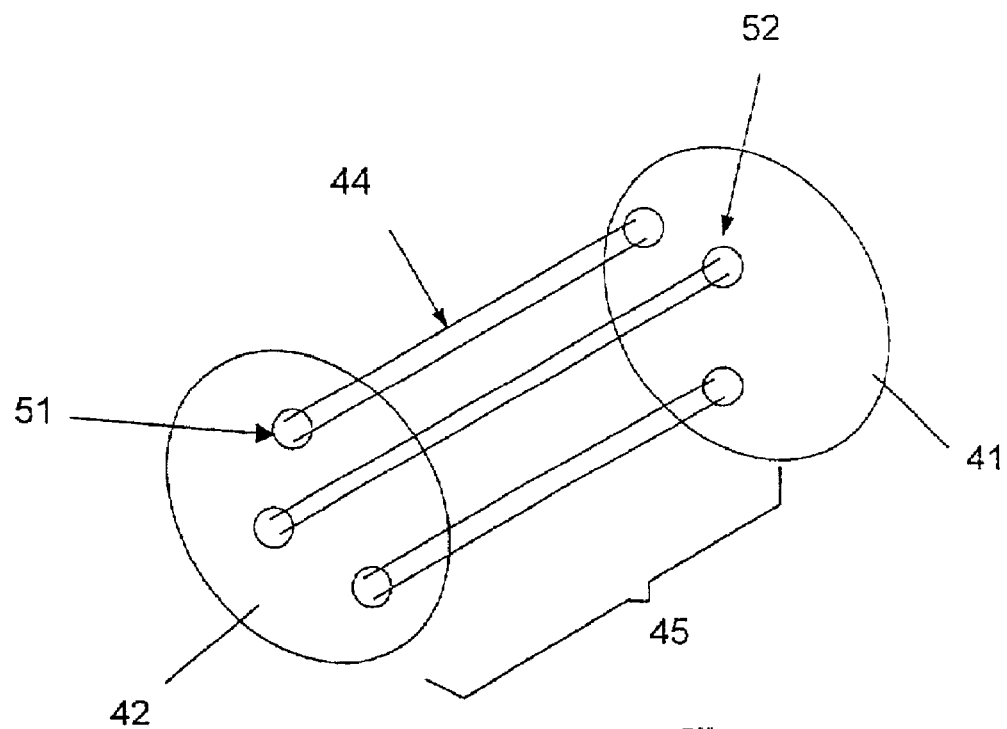
FIG. 7 schematically illustrates an alignment method based on intensity methods.

In another preferred embodiment of the invention, use is made of intensity measurements. This method is shown in FIG. 7 and requires the use of at least three transducers (designated by numeral 52) on the distal tip 41 and three (numeral 51) on the cartridge 42. To reach alignment, it is necessary to position all the three transducers on the distal tip in front of the three transducers on the cartridge. At first the distal tip is located somewhere in front of the anvil. The distal tip scans a spatial angle of 180° or less and the angle where the maximum amplitude was measured is stored. The distal tip is displaced according to the stored angle and the scanning recommences. This procedure is repeated until the maximum amplitude is measured, at each receiver when its mating transmitter is active at 0°.

There are several possible situations that could arise in the alignment procedure that must be taken into account when developing the methods that are used to process information on the position of the distal tip in front of the cartridge and then displace the distal tip in the direction of closer alignment according to this information. As an example, the distal tip is located above or below the cartridge, thus transverse scanning might not detect anything, but the up-down scanning will detect a signal (actually it might detect two signals, from the lower and the upper receiving transducers). Another example is when the upper transducer of the distal tip is located in front of (or close to) the two lower transducers of the cartridge. In this case transverse scanning will detect two positions and up-down scanning might or might not detect any signal.

In order to achieve maximum precision, it is necessary that the transmitting beams be as thin as possible. There are two ways of satisfying this requirement. A first embodiment, illustrated in FIG. 7, relies on the fact that in the Fresnel zone (designated by numeral 45) the beam (designated by numeral 44) is somewhat collimated and thin. Thus to maximize precision, the method is employed at distances less than the Fresnel distance=$r^2/\lambda$, where r is the radius of the transducer, $\lambda=v/f$ is the wavelength of the transmitted beam, f is the natural resonance of the transducer, and v is the speed of sound in the medium.

Figure 8:
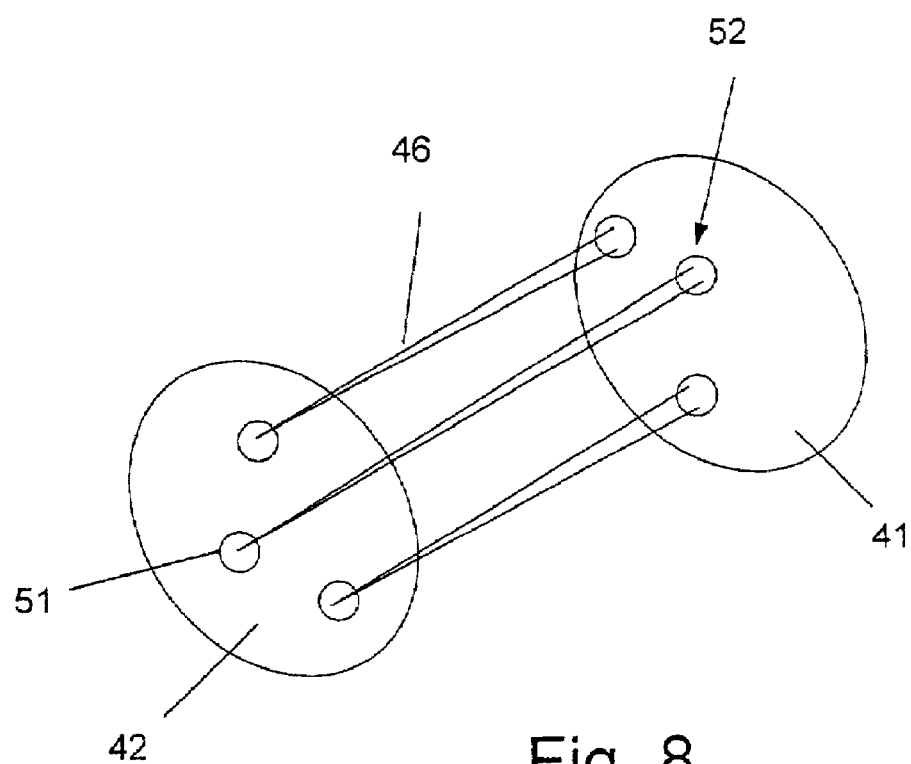
FIG. 8 schematically illustrates another alignment method based on intensity methods.

The second embodiment is shown in FIG. 8. Here, as in FIG. 7, the transducers are designated by numerals 51 and 52, the distal tip by 41, and the staple cartridge by 42. In this embodiment, the set of transducers that act as the transmitters, for example those on the distal tip, are focused transducers. This results in focused beams (numeral 46). For better precision, it is also possible to use focused transducers as receivers.

The desired resolution dictates that in both embodiments, optimal precision will be obtained at high frequencies (e.g., 10 MHz and above for a 1 mm radius transducer). It should be noted that in the Fresnel zone the transmitted intensities contain irregularities therefore, although the distal tip is moving towards the anvil there are points where the intensity will decline instead of increasing. This difficulty must be taken into account in designing the process referred to above.

Although in principle the above embodiments have the advantage of simplicity, the scanning procedure can consume a lot of time and also requires that the endoscope have scanning capabilities for the distal tip. In addition, the large number of transducers and the electrical wires that connect them require a large volume of a very limited amount of space and also increase the cost of the system.

If the transmitting and receiving transducers are located symmetrically, then the system will appear to be aligned even if a rotation of 120° in either direction takes place. This potential error can be avoided by, for example, using an asymmetric arrangement of the transducers or by causing each transmitter to generate a unique sequence of pulses.

Figure 9B:
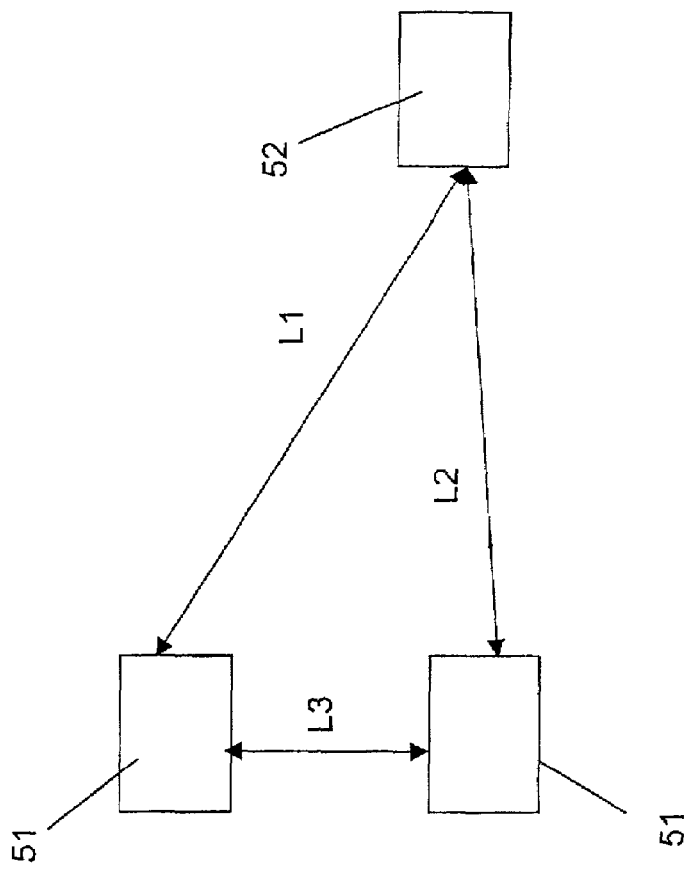
FIGS. 9A and 9B schematically illustrate a triangulation method of alignment.
Figure 9A:
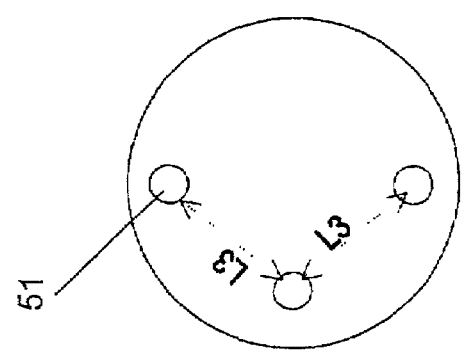

Embodiments of the invention, which improve on the above-described embodiments primarily by reducing the number of transducers required, are based on the principle of triangulation. The basic configuration employed comprises one transmitter and three receivers (or three transmitters and one receiver). FIG. 9A shows the array of three receivers (designated by numeral 51) located on, for example the stapler cartridge. The distance between every two receivers $L_3$ is known, since it is precisely defined at the production stage. Every two receivers and the transmitter create a triangle, thus alignment is achieved when the three triangles have equal sides, as determined by the desired distance between cartridge and tip. The distal tip is displaced until all the measured distances are equal. The displacement direction is evaluated from the differences between the three measured distances. It is also possible to construct the triangle asymmetrically such that for alignment detection the triangle will have unequal sides.

Limiting the number of degrees of freedom of the endoscope will reduce the amount of transducers, e.g., with a two-way endoscope, only one transmitter and two receivers will be used. The situation for a two-way endoscope is shown in FIG. 9B. In FIG. 9B, numeral 51 designates a transducer used to receive the signal transmitted by the transducer designated 52. As explained above, transducer 52 is moved until $L_1=L_2$, at which point the two parts of the stapler are aligned, and the distance is determined by one of the methods described previously.

The embodiments employing the triangulation method are improved upon by using transducers built from an array of elements instead of single element transducers. In this case multiple triangles are created and the measurements are therefore more precise.

Another difficulty that arises in using triangulation methods is that the beam in the Fresnel zone is sometimes very thin thus, it is impossible to illuminate two adjacent receiving transducers with only one transmitting transducer and vice versa. To overcome this difficulty a diverging transducer is used or an aperture is placed before the transmitting transducer causing the beam to be divergent and therefore assuring that the signals from the transmitter will reach the receivers. The use of diverging beams results in weaker signals and reduced alignment accuracy.

Figure 10:
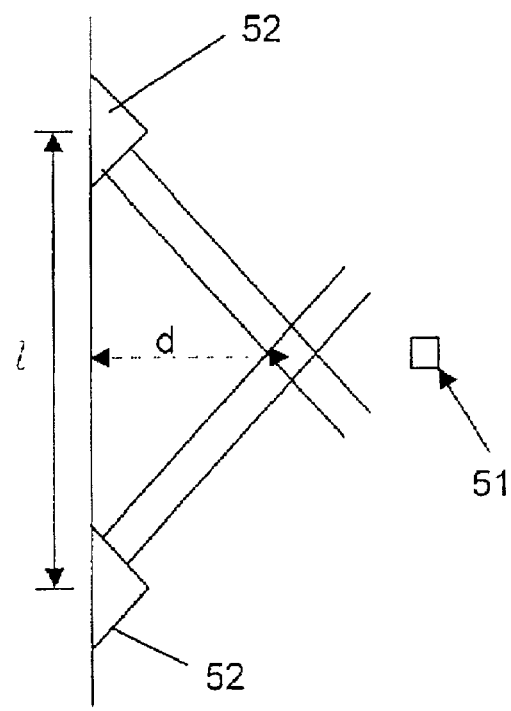
FIG. 10 schematically shows a triangular construction for use in an alignment method.

In another preferred embodiment of the invention, some of the difficulties encountered in the previously described embodiments are overcome by a special arrangement of the transducers employed in the triangulation measurements. The following description is given for a two-way endoscope, for the sake of simplicity, but can easily be expanded to a four-way endoscope by adding another triangulation construction. The triangulation construction shown schematically in FIG. 10 comprises two transmitters 52, with a distance l between them, and one receiver 51. The transmitters are mounted on the stapler cartridge at such an angle that the two transmitting beams meet at a distance "d" from the axis that is perpendicular to the cartridge. The distal tip scans the cavity until it locates (by intensity measurement) one arbitrary beam. Then the distal tip follows this beam by gentle scanning until it reaches the point where the received amplitudes from the two transmitters are equal. The transmitters transmit sequentially with a time interval. This method is limited to using thin beams and thus works in the range of a couple of MHz to insure that the meeting point will be in the Fresnel zone. Instead of working in the Fresnel zone it is possible to use focused transducers with focal length of the desired distance.

Figure 11:
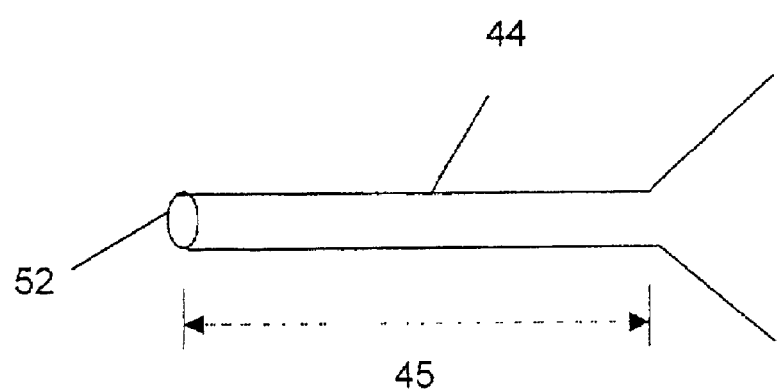
FIG. 11 schematically illustrates the shape of an ultrasound beam.

The fact that after the Fresnel zone or after the focal point the beams are divergent is useful in initially locating one of them from a distance where the cross section of the beam is larger than it is when close to alignment. FIG. 11 schematically shows the behavior of the beam 44 transmitted by the transducer 52. Within the Fresnel zone 45, the beam is essentially collimated; while beyond the zone, the beam diverges.

The following specific example illustrates possible dimensions used for building the triangle construction for the above-considered endoscope containing a stapler:

The distance between the distal tip containing the anvil and the stapler cartridge=d=4 mm.

The distance between the transmitting transducers=l=10 mm.

The radius of the transducer=a=1 mm.

Using the requirement that the Fresnel distance (=$a^2/\lambda$ for d>>a) should be longer or equal to d leads to the result that $\lambda=0.25$ mm, i.e. the frequency F=6.16 MHz. At 3 dB, the half beam angle θ is determined from, sin θ=0.51·λ/2a, yielding θ=3.65°. The angle is measured with respect to the perpendicular to the transducer surface, therefore the total angle 7.32°.

It should again be mentioned that, within the Fresnel zone, the intensity of the transmitted beam is described by a Bessel function and is therefore not uniform. This fact must be taken into account when using embodiments of the invention that are dependent on measurements taken within the Fresnel zone.

As discussed above, in an alternate embodiment focused transducers with a 4 mm focal point are used. In this case it is possible to carry out the measurements at higher frequencies.

The major advantage of this embodiment is that it omits the need for distance measurement, because the distance is a priori known from the special construction.

A further embodiment of the invention that reduces the complexity of building the precise triangulation construction and omits the mechanical scanning employs a phase array. This embodiment comprises a transducer mounted on the distal tip and two or more transducers mounted on the cartridge (or vice versa). The transducer on the distal tip is built from an array of elements (the ones on the cartridge can be built from one element or an array of elements). The array produces a beam that can be steered by electronic means. The steered beam scans the cavity until it is received by one of the transducers. The angle of the steered beam suggests the displacement direction of the distal tip. The alignment is achieved when the measured angles are equal (or can be pre-manufactured with known non-equal angles) to both transducers. In this embodiment the distance can be measured by time of flight or triangulation calculation. Another way of implementation is imitation of the triangulation construction described above with reference to FIG. 10. In this case mounting the transducers at an angle to the surface of the cartridge is not necessary since the steerable beam from the array replaces this feature.

Figure 12:
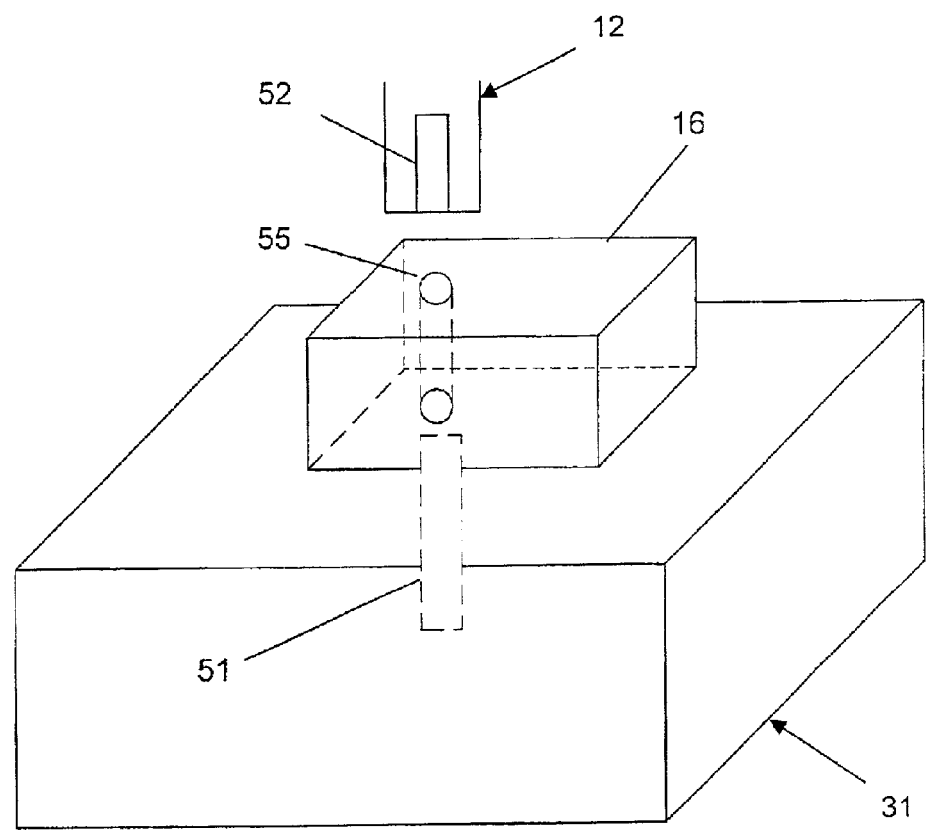
FIG. 12 schematically illustrates the wave-guide positioning method.

An alignment method based on intensity measurements, which is a greatly simplified version of the first alignment method described above, is illustrated schematically in FIG. 12. This embodiment employs two transducers. The transducer 52 on the distal tip 12 is the transmitter. The receiving transducer 51 is mounted on the cartridge holder 31 below the movable staple cartridge 16. A channel 55, which is created throughout the entire height of the cartridge, guides the signal to the receiver. The channel has a small diameter of about 0.5-1 mm. This configuration detects alignment only when the distal tip is positioned in exactly the right position in front of the cartridge.

The preferred embodiments of the invention are based on systems that comprise one transducer and either a single reflector or a plurality of reflectors. The transducer is used both for transmitting and receiving. The reflector is built from a special construction that reflects back a pattern that can be translated into the position and orientation of the transmitter relative to the reflector. The transducer can be mounted on the distal tip or on the staple cartridge or vice versa. Mounting the reflector on the cartridge is usually preferred, since this eliminates the electrical wire connections for the transducer that would interfere with indexing of the cartridge. The following are representative, but not limitative, examples of the many possible configurations that can be derived from this model.

Figure 13A:
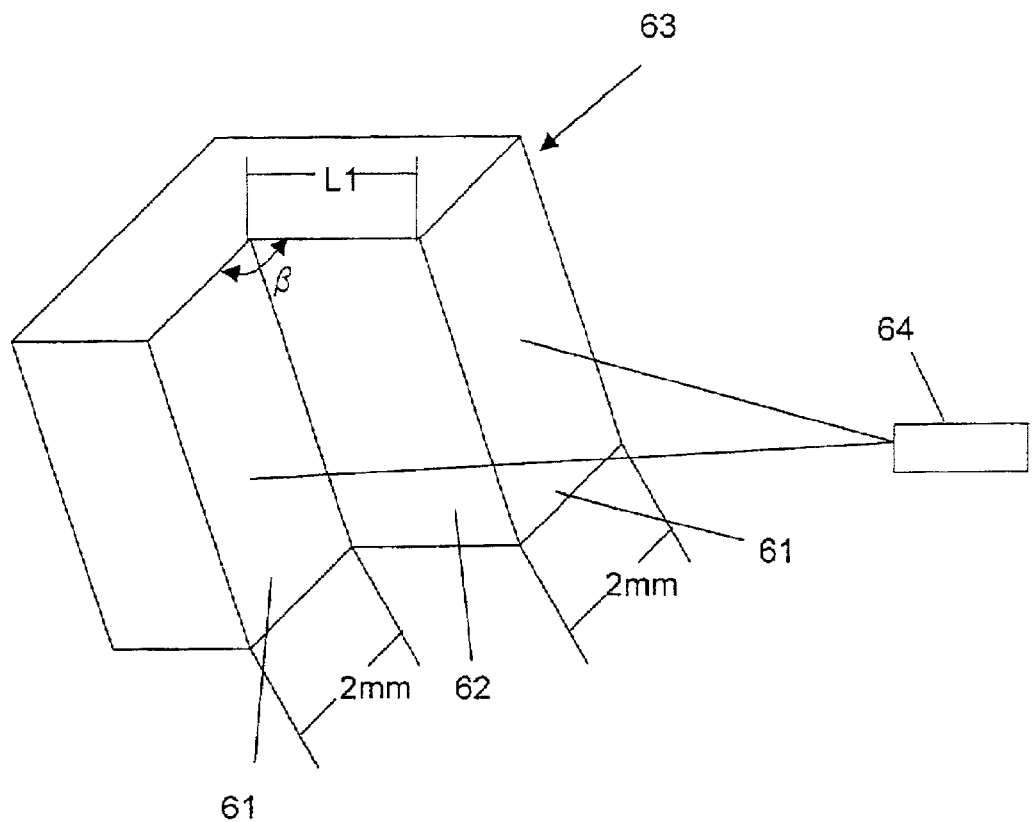
FIG. 13A schematically illustrates a one-step reflector.
Figure 13B:
FIG. 13B schematically illustrates the signal reflected from the reflector of FIG. 13A.

The basic configuration (including representative dimensions) of these embodiments is shown in FIG. 13A. Two parallel reflecting planes (designated by numeral 61) are separated by a distance $L_1$ by a planar surface 62 that intersects the reflecting surfaces at an angle β such that β≦90°. The resulting step construction (generally indicated by numeral 63) is irradiated by the beam from the transmitting transducer 64. If the transmitted beam impinges on both layers, then the reflected signal comprises two consecutive echoes, one from the front layer and the second from the rear layer as shown schematically in FIG. 13B.

Figure 13C:
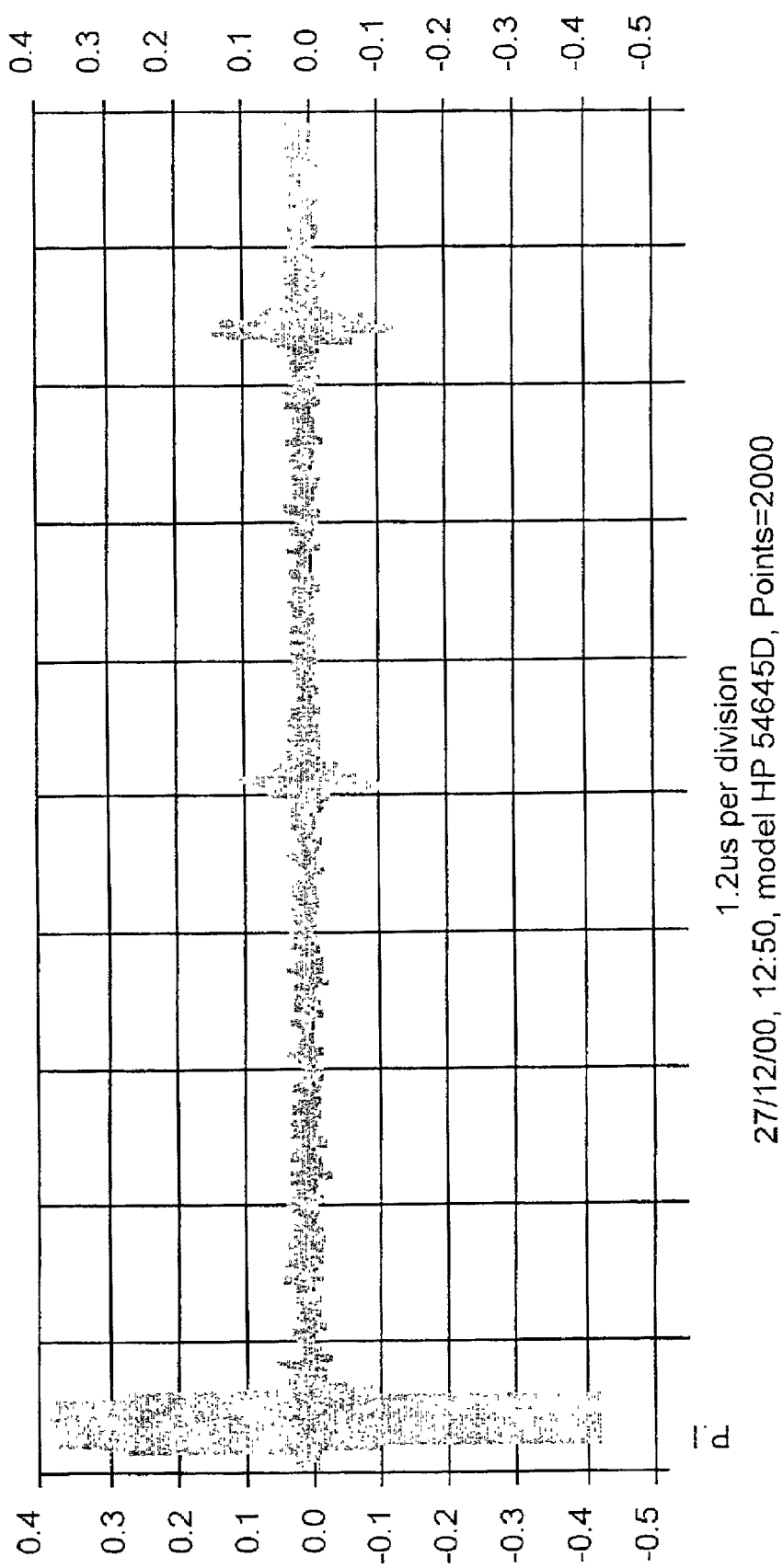
FIG. 13C is a reproduction of an oscilloscope screen showing the reflections from a reflector of the type shown in FIG. 13A.

FIG. 13C is a reproduction of a photograph of an oscilloscope screen showing the results of an experiment carried out using a one-step reflector of the type shown in FIG. 13A. The large pulse on the left of the screen is the transmission pulse and the two smaller pulses are the echoes from the reflector. In this example, the reflector is positioned such that the nearest reflecting surface is 4.3 mm from the emitting transducer and the depth of the step $L_1$=3 mm. The measured time between the pulses is 4.08 μsec, thus the measured depth of the step is found from $$L_1 = d = \frac{v_c \times t}{2} = \frac{1500 \text{ m/s} \times 4.08\mu \text{ sec}}{2} = 3.08 \text{ mm}$$

The agreement between the measurement and the actual depth is determined by the measuring system performance. Methods of improving the agreement will be discussed below in conjunction with the descriptions of the software and the electrical module.

When the transducer is aligned with the reflector then the measured distance between the layers must be $L_1$ and the measured pulses must have an amplitude relation that is relative to the depth of the step. This relation can be evaluated from the well-known attenuation relation of an ultrasound wave propagating in soft tissue (G. S. Kino, Acoustic waves: devices, imaging and analog signal processing, New Jersey: Prentice-Hall Inc., 1987.)

$$\frac{A_{rear}}{A_{front}} = -2 \times 0.8 \text{ dBcm}^{-1}\text{MHz}^{-1},$$

Where $A_{rear}$ is the echo amplitude from the rear layer and $A_{front}$ is the echo from the front layer. Other influences on the signal amplitude are the step cross-section and the spatial angle between the distal tip and the reflector face. For example, consider the two-echoes reflector described with relation to FIG. 13C that reflects back a signal emitted from a transducer with a natural frequency of 10 MHz (a 100 nsec pulse). The relation $A_{rear}/A_{front}$ yields approximately 4.8 dB or $A_{rear}$=0.707$A_{front}$. Referring to FIG. 13C, the front echo amplitude is smaller than the rear echo suggesting that alignment has not been achieved. Furthermore if for instance the path of the transducer on the distal tip dictates that it should irradiate the front reflective layer first and then, after, the rear layer then it is obvious that the distal tip should be moved back in order to achieve alignment.

The detection procedure that is used to implement the alignment is based on the following criteria:
1. Alignment is accomplished only when the echoes are received at a certain time difference and with a certain amplitude relation (within predefined, reasonable tolerances).
2. The reflector and the transducer are not aligned whenever:
   no signal is received, or
   only one echo is received, or
   the amplitude relation is not satisfied, or
   the time between the consecutive echoes is different (i.e. a different distance is measured).

This procedure will be discussed hereafter in more detail.

Figure 14A:
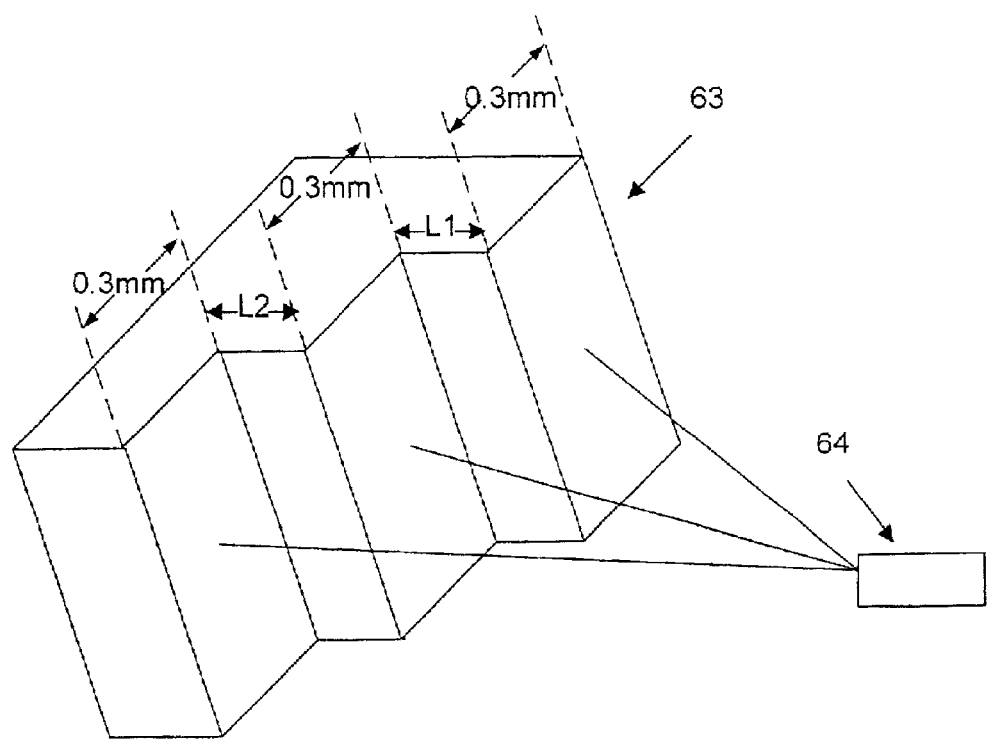
FIG. 14A schematically illustrates a two-step reflector.
Figure 14B:
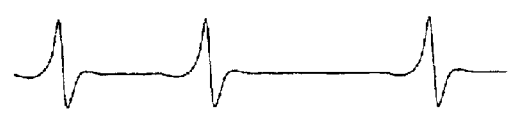
FIG. 14B schematically illustrates the signal reflected from the reflector of FIG. 14A.
Figure 15A:
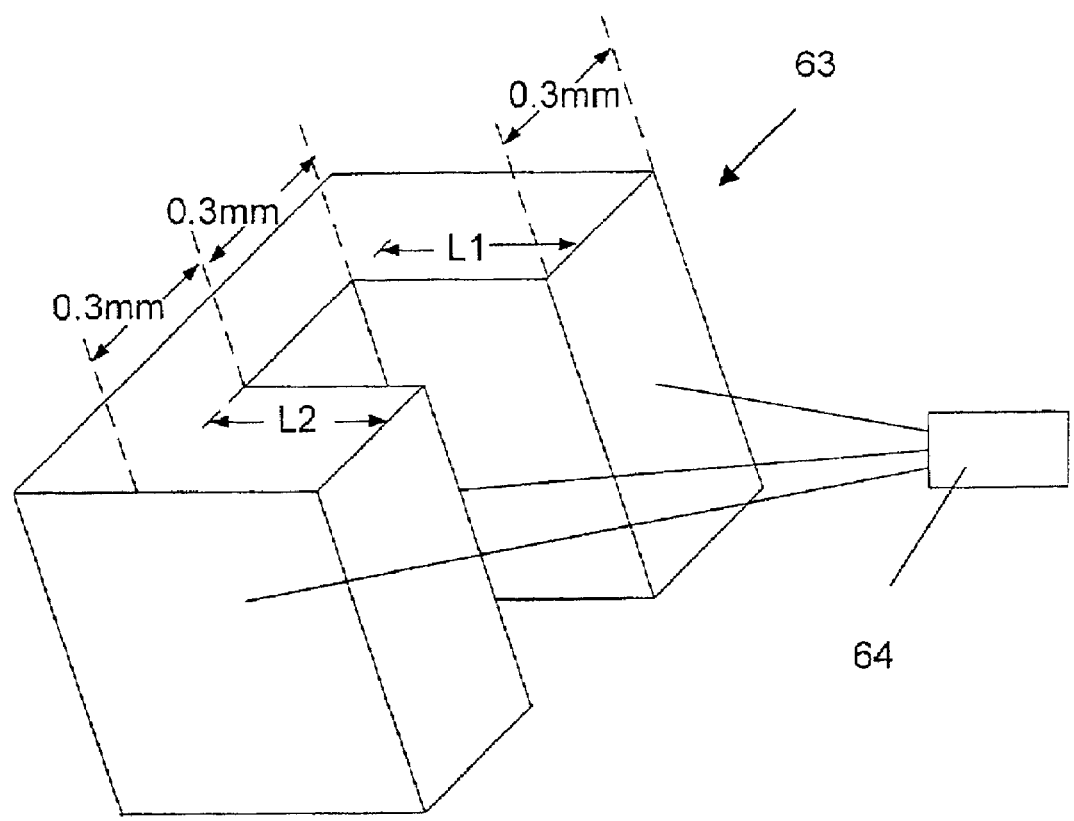
FIG. 15A schematically illustrates another two-step reflector.
Figure 15B:
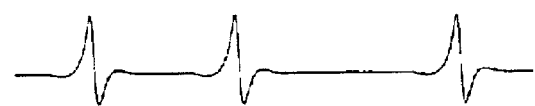
FIG. 15B schematically illustrates the signal reflected from the reflector of FIG. 15A.
Figure 16A:
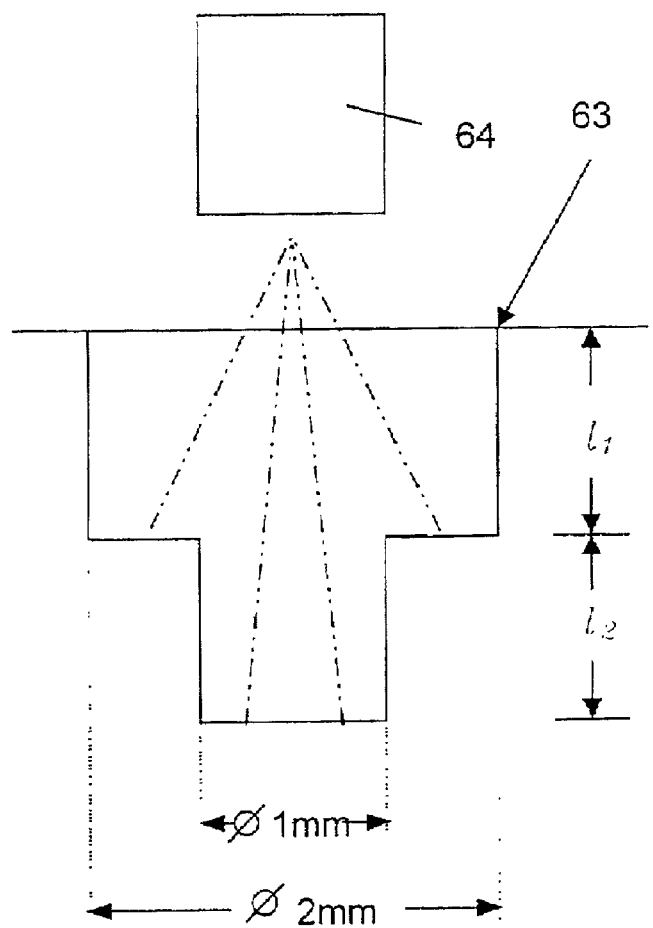
FIG. 16A schematically illustrates a cylindrical reflector.
Figure 16B:
FIG. 16B schematically illustrates the signal reflected from the reflector of FIG. 16A.

In a preferred embodiment of the invention, the reflector is constructed with two or more steps. FIGS. 14A, 15A, and 16A illustrate a few of the many possible two-step (three echoes) constructions that can be used. In these figures, the reflector is generally designated by numeral 63, the transducer by 64, $L_1$ and $L_2$ are the heights of the two-steps, and typical dimensions are shown. In these cases the reflected signal comprises three echoes with certain time differences and amplitude relations between them that correspond to $L_1$ and $L_2$ respectively. The reflected signals that correspond to 14A, 15A, and 16A respectively are schematically shown in FIGS. 14B, 15B, and 16B.

Using different values of $L_1$ and $L_2$ assists in completing the alignment. If for instance, only two of the three echoes are received, it is possible to determine on which pair of steps the beam of the transducer is falling by the distance between the echoes. This information is then used to determine the position of the distal tip relative to the reflector and to steer it closer to alignment.

FIG. 16A shows a two-step reflector made from a cylinder with two bores drilled inside. One bore is 2 mm diameter and in the center of the 2 mm bore another 1 mm bore is drilled. This construction when almost, but not exactly, aligned will reflect back three consecutive pulses; one from the face of the reflector one from the peripheral area of the 2 mm bore and the third pulse is from the bottom of the 1 mm bore. There will be two-echoes when the parts are exactly aligned or if the displacement is such that the bottom of the 1 mm bore is not irradiated by the transmitted beam. To distinguish between the possibilities when only two-echoes are measured, the reflector is constructed with steps of unequal depth.

Figure 16C:
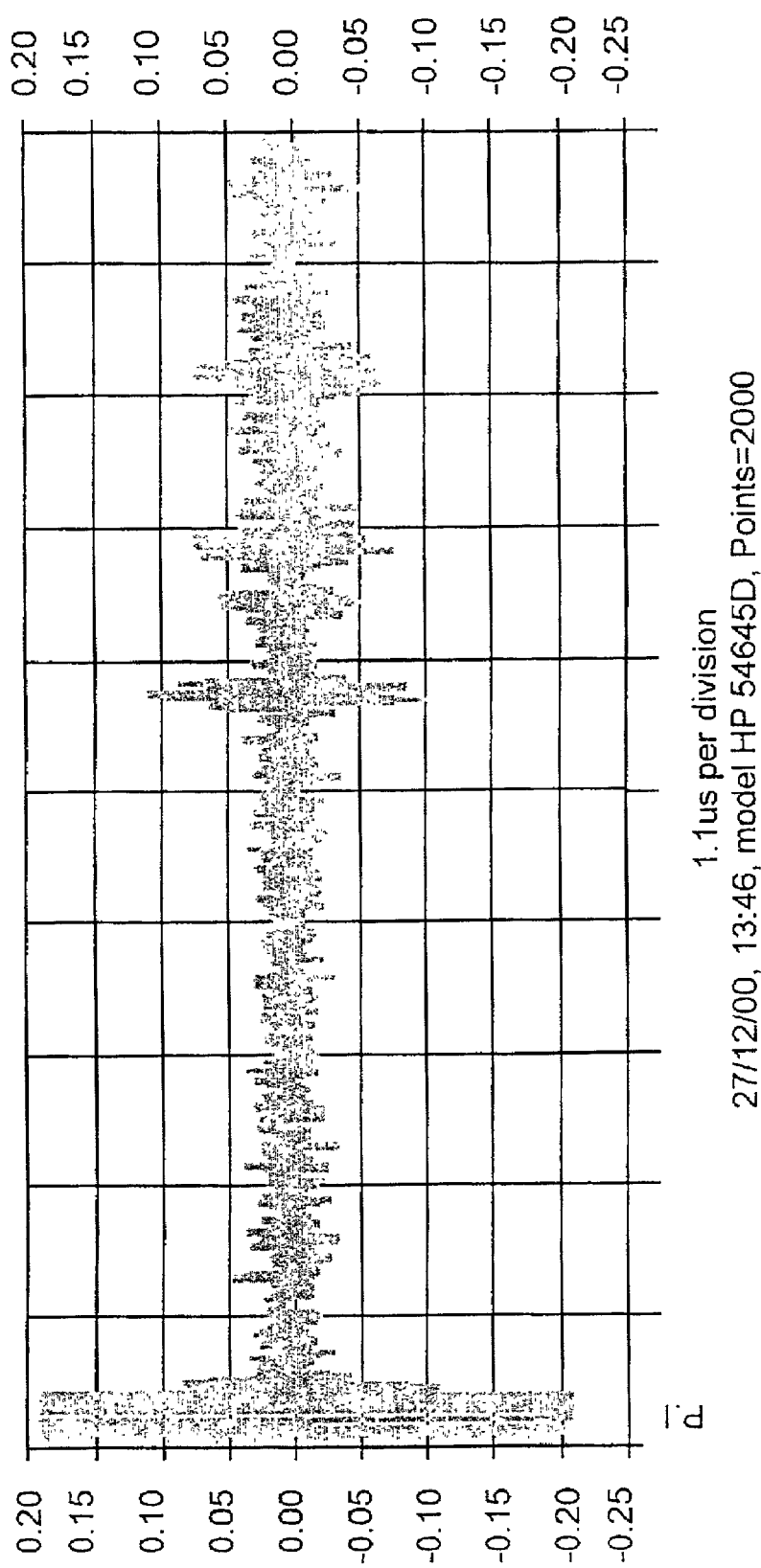
FIG. 16C is a reproduction of a photograph of an oscilloscope screen showing the reflections from a reflector of the type shown in FIG. 16A.

FIG. 16C is a reproduction of a photograph of an oscilloscope screen showing the results of an experiment carried out using a two-step cylindrical reflector of the type shown in FIG. 16A. The left signal is the transmitting pulse; the three echoes on the right are from three different layers. The depths between the layers are $L_1=L_2=1$ mm. The reflector is mounted 4.7 mm from the reflector. The measured time between the consecutive echoes is 1.3 μsec, thus the calculated depth is $$L_1 = L_2 = d = \frac{v_c \times t}{2} = \frac{1500 \text{ m/s} \times 1.3\mu \text{ sec}}{2} = 0.975 \text{ mm}$$

Figure 24:
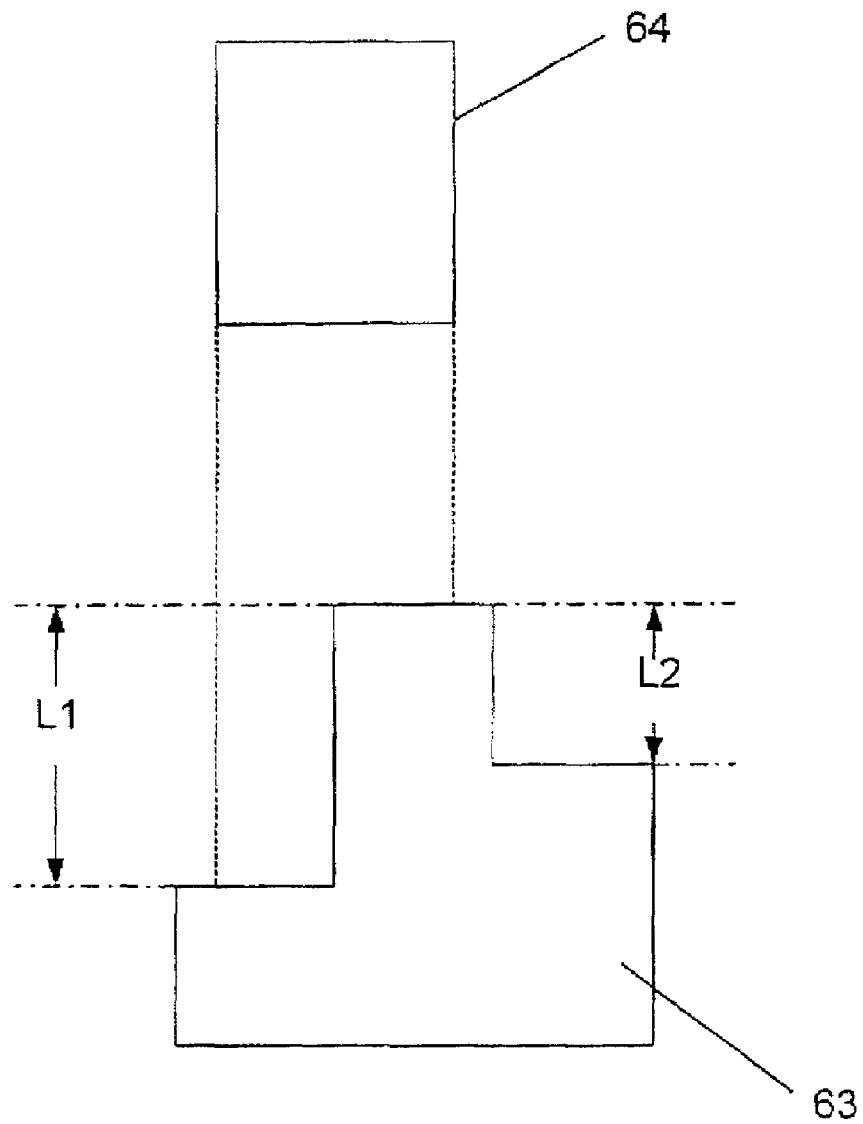
FIG. 24 schematically illustrates a two-step reflector.

Another procedure that forms a part of the present invention uses a displacement algorithm. This algorithm can be implemented only on two (or more) step (or bore) reflectors, i.e. a minimum of three echoes are required. In this embodiment, the reflector is built with different size step depths. If the emitted transducer spot falls on only some of the steps, then only some of the echoes will be received. The following example, described with reference to the step construction of FIG. 24, reveals the basis of the algorithm. FIG. 24 shows a two-step reflector 63 having two distinct step depths $L_1 \neq L_2$. The transmitting/receiving transducer is designated by the numeral 64.

For alignment detection, it is necessary to receive three echoes. In FIG. 24, the transducer is placed left of the aligned position. Therefore only two-echoes are received. Since the displacement algorithm calculates that the distance between the echoes is $L_1$, the algorithm will suggest to the operator to displace the transducer to the right until three echoes are received.

FIGS. 25A through 25F further illustrate the principles of the alignment procedure. In FIGS. 25A, 25B, and 25C a two-echo (one-step) reflector of the invention 63 is irradiated by a transducer 64.

FIG. 25B shows the relative positions of the transducer and reflector when the system is aligned. In FIG. 25E, which schematically shows the corresponding received signal, a fixed relationship exists between the echoes from the two reflecting surfaces. In FIG. 25A, the transducer has "overshot" alignment and, as shown in FIG. 25D, the required ratio between the two-echoes does not exist, i.e. the echo from the farthest surface is much larger than from the closest surface. FIGS. 25C and 25F illustrate the situation in which the transducer has "under-shot" alignment. It should be clear to the skilled engineer how the operator can use this information to steer the elements into the correct alignment. The above procedure is the basis for the development of a process to automate the alignment procedure.

FIG. 17 schematically shows the preferred embodiment of the invention applied to a stapler which may be, e.g., that disclosed in PCT/IL01/00719. The stapler cartridge is generally shown at 16. Numeral 71 designates each of the three arrays of five staples each and numeral 72 designates two-step reflectors that are created into the surface of the cartridge next to each array of staples. As an example, typical measurements are shown on one of the reflectors. In this embodiment, the transducer is located on the distal tip of the endoscope at, for example, one of the positions 23 or 26 in FIG. 4. Many other possibilities exist for constructing the reflectors as an integral part of the cartridge. For example, in another preferred embodiment of the invention, the reflectors are created as a set of steps that protrude above the surface of the cartridge. The implementation of the methods of this invention in the case of four-way endoscopes has to be somewhat different then those for two-way endoscopes in order to include the effects of rotation. In one preferred embodiment of the invention for use with a four-way endoscope, a reflector is mounted on the cartridge and a transducer on the distal tip. If the distal tip is rotated relative to the reflector, then (as long as the transducer is not located at the center of the distal tip) the transmitted beam will not fall on the steps of the reflector and the reflected beams will not be detected.

Another preferred embodiment of the invention, for use with a four-way endoscope, makes use of two reflectors mounted on the cartridge. In this embodiment, the reflectors are mounted perpendicularly to each other. The depths of the steps of the two reflectors are different. Therefore it is possible to determine which of the reflectors is being irradiated by the transmitted beam. This information is incorporated into an algorithm to correct for the rotation and to bring the parts of the stapler into proper alignment.

In designing the reflecting elements employed in the above-described embodiments of the invention, several factors have to be taken into consideration. Among these considerations are the following:

1. The probability that echoes, with a certain time difference between them and with a certain amplitude relation, will be reflected back from the ambient area is very small. The probability is greatly reduced by using more than two echoes making the constructions that give rise to three echoes the preferred embodiments of the invention.
2. In order to receive high amplitude echoes, it is best to use step widths as wide as possible. In two-echo (one-step) reflectors the step width is unlimited. However, in three or more echo reflectors, it is very important that the accumulation of all step widths not exceed the beam width to insure that there are reflections from all of the surfaces when alignment is achieved. On the other hand, making the step widths excessively narrow will result in very weak amplitude reflections.
3. The height of the steps (i.e. the distances between the reflecting layers) must be more than the resolution of the measuring system i.e , it is best to design the step depth such that it is greater than the length of the echo duration multiplied by the speed of sound in the tissue (for example 1500 m/s) divided by 2. It is possible to work with depths less than these; but, in this case, the reflected echoes will be partially overlapping causing lower signal-to-noise ratio 4. In some cases it is possible to surround the reflecting surfaces with absorbing material and thus, to increase the contrast of the reflector.

5. One of the possible sources of inaccuracy in the use of multi-step reflectors is the air gaps that can be created if the tissue is not in firm contact with all of the reflecting surfaces. One possible solution to this problem is to fill the gaps with medical ultrasonic gel. The conventional gel is often displaced during insertion of the endoscope; therefore it is preferred to fill the steps with a hard or flexible material having acoustical matching to the tissue. In this case no air gaps are created and therefore no error will occur in the measurements. A suitable material for this purpose is, for example, industrial silicon or commercially available bio-compatible silicon products well known in the art, such as GE silicon RTV 108. When a silicone layer is used reflections will take place from the face of the silicon as well as the metal cartridge case; thus, if the silicon is applied with two layers having different thicknesses, a step-type reflector will be created and the pattern of the reflected echoes can be used to determine the position of the distal type with respect to the cartridge.

6. Transducers with many different characteristics can be employed in the various embodiments of the invention described above. An example of a transducer used in the preferred embodiment of the invention is a single element, directional transducer that is capable of both transmitting and receiving. The diameter of the transducer is one mm and its length is two mm. The connecting cable has a diameter of less than one mm. The device has a center frequency of 11 MHz and bandwidth (−6 dB) of 60%. The transducer is used in direct contact with the tissue and no matching layer is needed. The transducer is custom made for the Applicant by Blatek Inc., State College, Pennsylvania, USA.

The ultrasound circuit used to perform the distance and alignment measurements of the invention will now be described. The circuit can use either A-mode (one transducer for transmitting and receiving) or C-mode (two different transducers are used one for transmitting and one for receiving) scanning, without the imaging part. For the sake of brevity, the following description will be for A-mode but all the same principals can be implemented with the C-mode using the essentially the same electronic components and circuit.

In order to more clearly describe the invention, illustrative but not limitative examples will be presented as applied to the GERD surgical procedure carried out with the stapler-containing endoscope of the aforementioned co-pending International Patent Applications PCT/IL01/00238 and PCT/IL01/00719.

Figure 18:
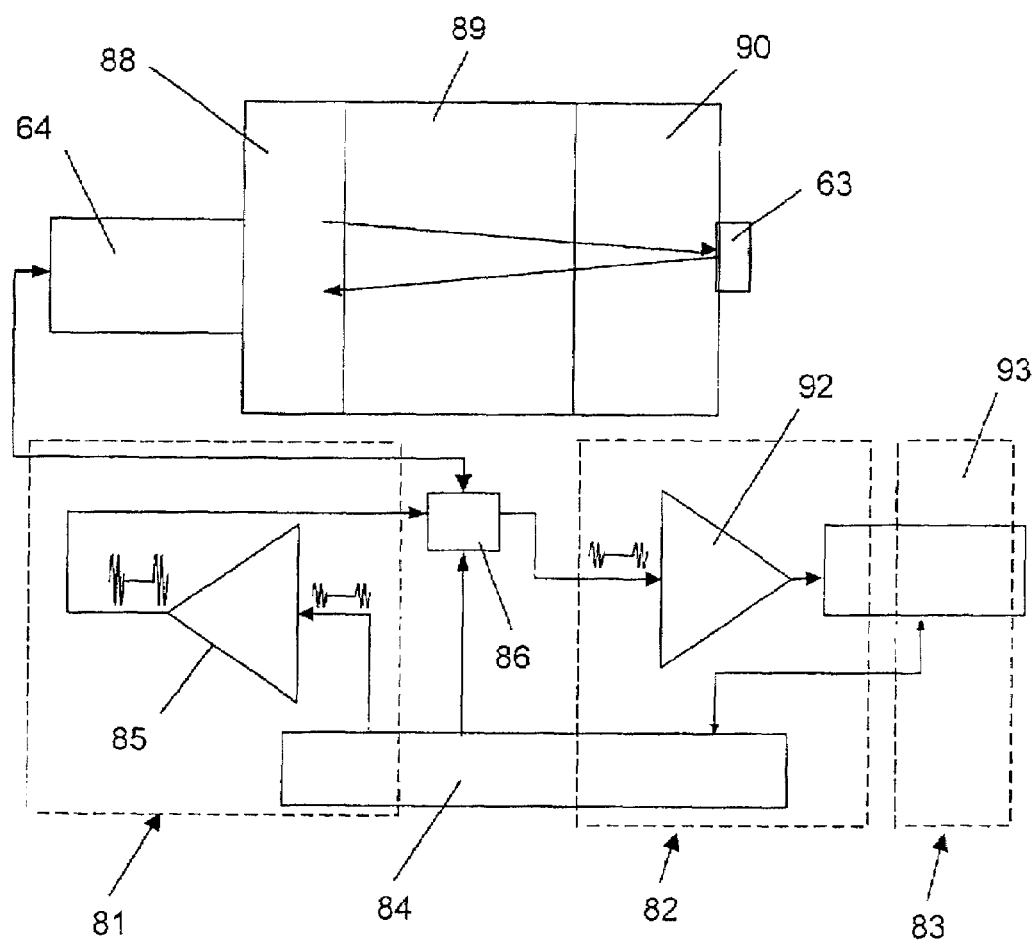
FIG. 18 is a block diagram of the ultrasound system.

FIG. 18 is a block diagram of the ultrasound circuit which is composed of three interconnected units: the transmitter (generally shown at 81), the receiver 82, and the digitizing, signal processing (DSP), distance and alignment unit 83. Numeral 84 represents the timing and control circuits and the input/output (I/O) interfaces. The timing circuit generates one pulse or burst of pulses of frequency of, for example, 11 MHz and with a pulse repetition rate (PRF) (or frequency) of 100 Hz. These pulses are amplified by a power amplifier 85 and applied through a transmit/receive (T/R) switch 86 to a transducer or array of transducers 64 that is, for example capable of both transmitting and receiving ultrasonic signals (equivalent to 52 in FIG. 7, where the transducer is a transmitter only). The transducer converts the electric signal to an ultrasonic signal. In order to integrate the transducer with the endoscope, the dimensions of the transducer must be very small. In a preferred embodiment of the invention, these dimensions are 1 mm diameter and 2 mm length and the cable that connects the transducer to the electric circuit is a coaxial wire with less than 1 mm diameter. The transducer lobe is directional and since it works within the Fresnel zone it is essentially collimated. The emitted sound wave penetrates the boundary of the stomach 88, then passes through the fat tissue 89, and finally enters the esophagus 90. In the esophagus, the sound wave falls upon a very good reflector 63 (or receiving transducer equivalent to 51 in FIG. 7) that is mounted on (or is part of) the staple cartridge. (In C-mode a transducer replaces the reflector). The reflected signal returns along the same path until the transducer receives it and transforms the ultrasonic signal to an electrical signal. The electric signal then passes through the T/R switch 86 to amplifier 92, which amplifies the return signal from the transducer. The amplified signal then passes to an A/D device (located at 93, which also represents elements of the system that perform the DSP functions) to be digitized in order to implement carrying out digital signal processing.

The DSP module has two main functions:

1. To measure the distance between the distal tip and the anvil.
2. To confirm alignment between the distal tip and the anvil.

The digitization must meet the well-known Nyquist criteria but, because the signal is narrow band, it is possible to use under-sampling and thus decrease calculation loads and omit some electrical circuits.

Figure 19:
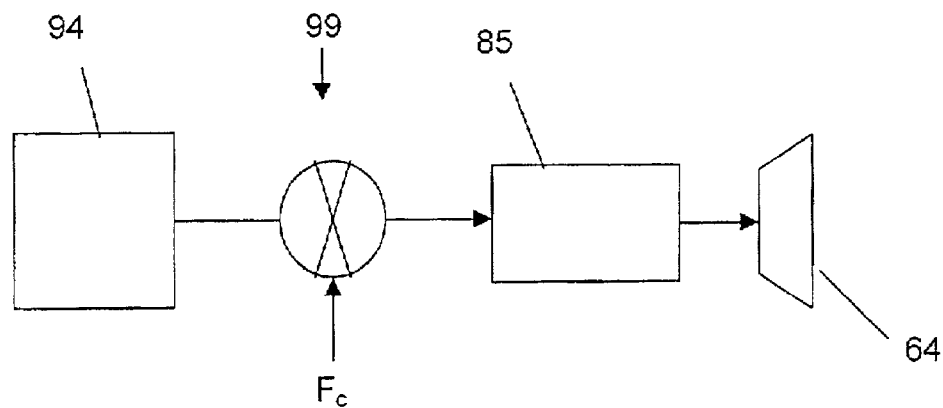
FIG. 19 schematically illustrates the transmitter portion of the ultrasound system.

The three main units of the ultrasound system of FIG. 18 will now be discussed in more detail. The transmitter unit is schematically shown in FIG. 19. The data bit generator and gate 94 are able to generate one pulse or bursts of data bits. They also determine the type of modulation of the carrier frequency Fc (which is a square or sinusoidal wave with an oscillation rate of, for example, 10.7 MHz) that is fed into the mixer 99. When transmitting one pulse only, the length of the pulse is determined by the transducer specification (in this example 100 nsec), and the pulse repetition frequency (PRF) is 100 Hz. By transmitting a burst of pulses or a random sequence of pulses or a modulated random burst of pulses it is possible to increase the reliability of the measurements and to work with very weak signals in a very noisy environment. The mixed (modulated) signal is transferred to the power amplifier 85 that filters and amplifies it before passing it to the transducer 64, which converts the electrical energy into ultrasonic energy.

Figure 20:
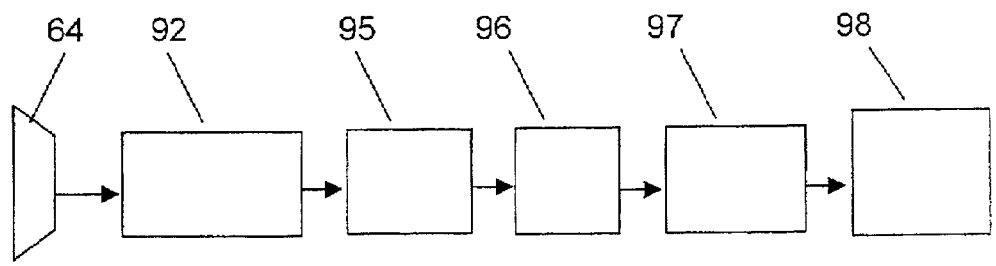
FIG. 20 schematically illustrates the receiver portion of the ultrasound system.

The receiver unit is schematically shown in FIG. 20. The ultrasonic wave that passes throughout all the tissues is received by the transducer 64, which converts the ultrasonic energy into electric energy. The signal is amplified by amplifier 92 and filtered by band pass filter (or filters) 95 to eliminate any undesired frequencies. Then the signal is digitized with an analog-digital (A/D) unit 96 (which has, for example, 8 bit resolution and a sampling rate of 100 MHz). Since the sample rate is very high compare to the data transfer rate of the computer, then it is necessary to use a fast first-in-first out (FIFO) unit 97 that stores the data until it is passed to the main memory 98 of a personal computer (PC).

The digitization module is a PC card that includes an A/D unit with a sample rate of 50-100 MHz. When transmission is initiated, the A/D unit simultaneously starts to sample and the data is collected in the FIFO unit for about 20 μs (which is equivalent to a distance of about 3 cm) and then the data is transferred to a buffer in the computer main memory.

The preferred method for implementing the distance calculations involves the use of the following correlation algorithm. The sampled data in the buffer is cross-correlated with a predefined signal pattern that is stored in the computer memory.

Figure 21A:
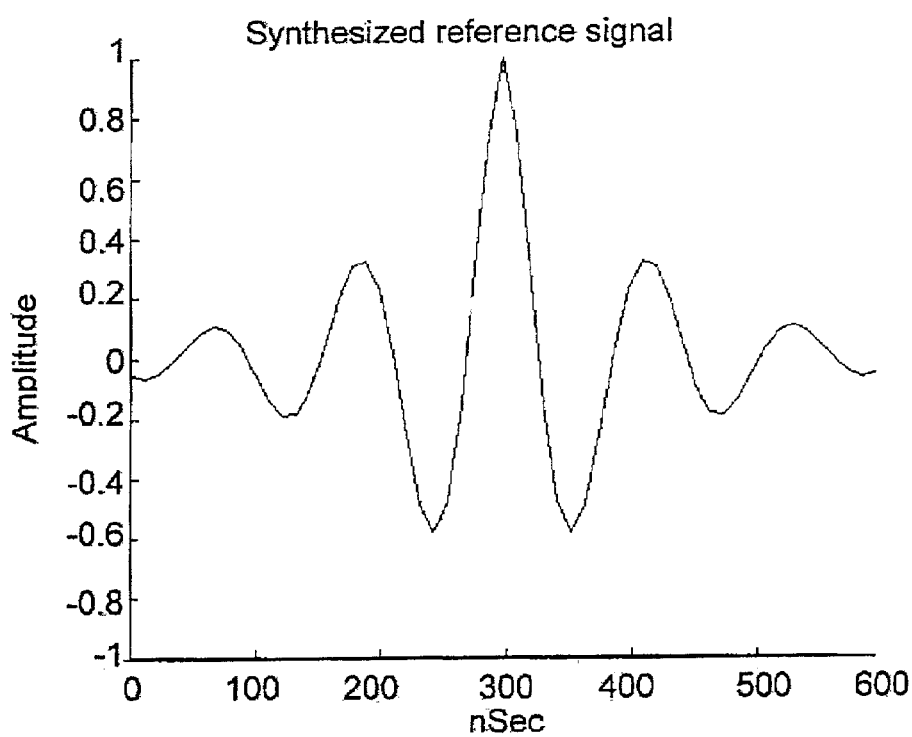
FIGS. 21A and 21B are reproductions of photographs of computer screens showing predefined reference signals.

The reference signal can be created in two ways. The first method makes use of the fact that it is possible to synthesize or to write a function that will generate the pattern of the reflected echo. An example of a function that generates such a reference signal is:

$$\text{ref}(t) = Ie^{-\tau t}\cos(\omega_d t - \theta) \, t \geq 0$$

$$\text{ref}(t) = Ie^{\tau t}\cos(\omega_d t - \theta) \, t \leq 0$$

where, τ is the dumping factor derived from the transducer specification, $\omega_d$ is the dumped natural frequency derived from the transducer specifications, and θ is a phase correction, if necessary (William W. Seto, Acoustics, Schaum's Outline Series, McGraw-Hill Inc., USA, 1971). FIG. 21A is a reproduction of a computer screen showing an example of a predefined signal calculated using the above formula.

It follows from the above that the accuracy of the measurement is determined by the sampling frequency, i.e., the error in the time measurement will be ±1/$T_s$. For example, if the sample rate is 100 MHz. Then, 1/100 MHz×1500 m/s=15 μm i.e., the accuracy in the distance is ±15 μm.

Figure 21B:
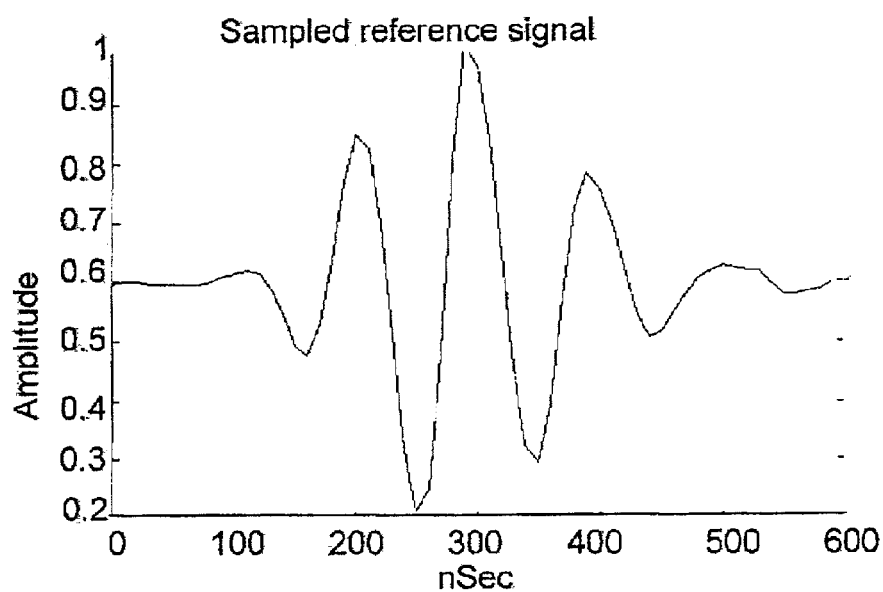
Figure 22A:
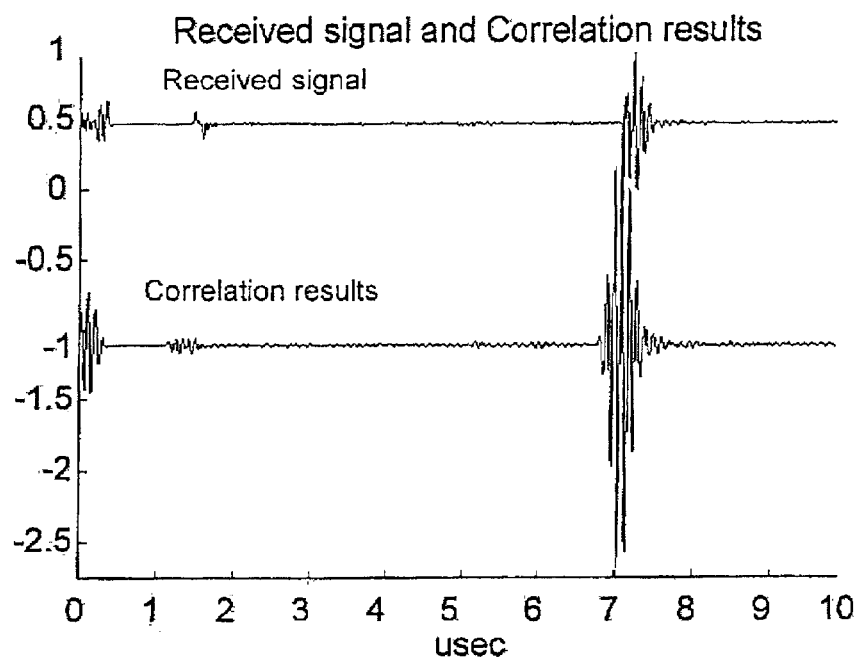
FIG. 22A is a reproduction of a photograph of a computer screen showing a measured received signal and a correlation result between the received signal and the reference signal of FIG. 21B.
Figure 22B:
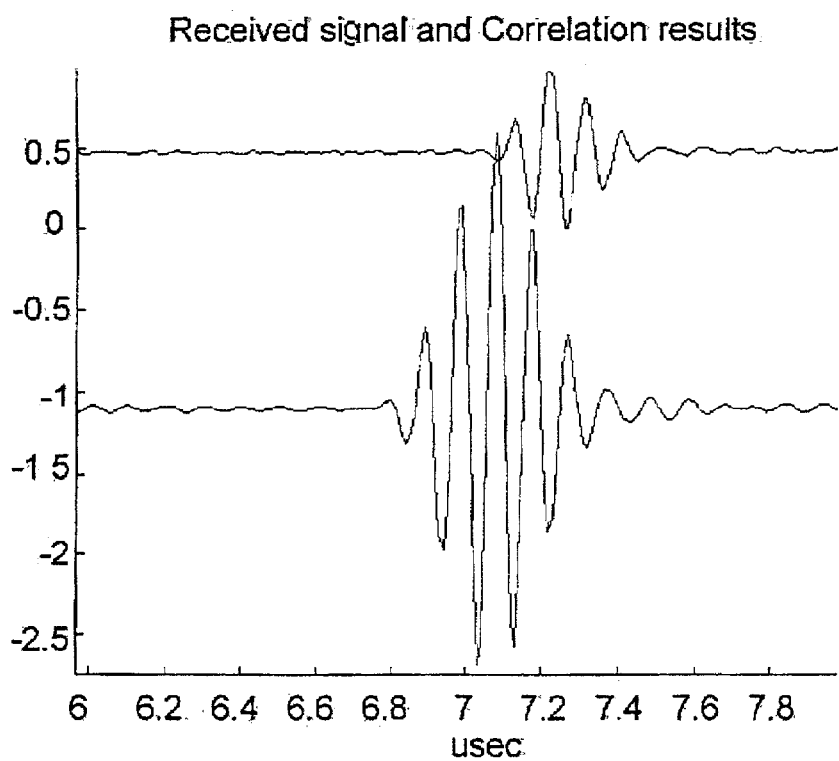
FIG. 22B is an enlargement of a section of FIG. 22A.

FIG. 224 is a reproduction of a computer screen showing the correlation results (lower curve) for a typical buffer between the received echo from a reflector (upper curve) and the pre-measured reference curve of FIG. 21B. FIG. 22B is an enlargement of part of FIG. 224 showing more detail of the received signal and correlation results. The maximum of the correlation occurs exactly at the beginning of the received signal.

The alignment algorithm uses the distance measurement algorithm as one of the criteria for alignment detection. The following example is for a onestep (two-echo) reflector, but it can easily expanded to cover the cases of reflectors having three or more echoes. The signal received in the buffer is correlated with the reference signal. Then the algorithm searches for the location of two maxima of the correlation. The distance between these two maxima must equal the depth of the step. If this criterion is not met then the transducer and reflector are not aligned.

In the second method an actual echo is sampled and stored in the computer memory for use as the reference signal. The second method is preferred, since it includes exactly the characteristics of all of the transmitting and receiving system including those of the transducer. Thus if, for example, the transducer (or any other component of the system) is replaced with another part having slightly different characteristics; it is possible to store the exactly expected reference signal in the computer memory by making a simple calibration measurement (for example in water). FIG. 21B is a reproduction of a computer screen showing an example of a premeasured reference signal. A cross correlation result is obtained from the following formula:

$$r_{ref,sig}(l) = \sum_{n=1}^{N-1} ref(n-l) \cdot \text{signal}(n) \quad 0 \leq l \leq N-1$$

where $r_{ref,sig}(l)$ is the cross correlation result, ref(n−l) is the reference signal and signal (n) is the received signal, N=length(signal)−length(ref).

The index of the element that contains the maximum in the correlation buffer ($r_{ref,sig}(l)$) corresponds to the place where the reference signal and the received signal best match. The time of arrival of the echo is calculated by $T_{arrival}$=(Buffer_index*1/Ts)/2, where Buffer_index is the index of the buffer where the maximum correlation is obtained and Ts is the sampling frequency.

If the distance between the maxima is correct, then the energy of the two echoes is compared to either meet the attenuation and area cross-section relationships heretofore presented or a pre-measured relation known from a calibration measurement. If these relations are not satisfied, then the alignment is not correct.

Figure 23:
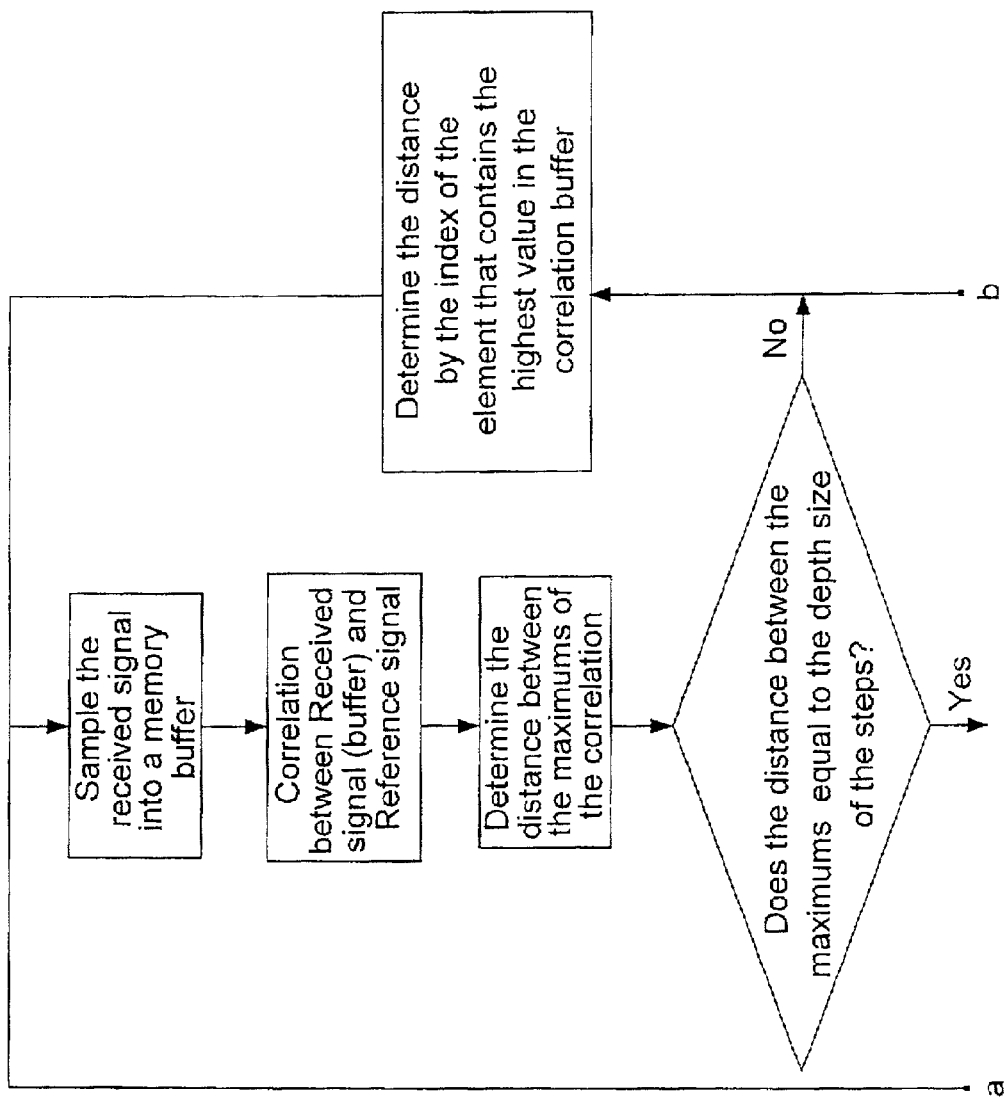
FIG. 23 is a flow chart of the alignment algorithm.
Figure 23:
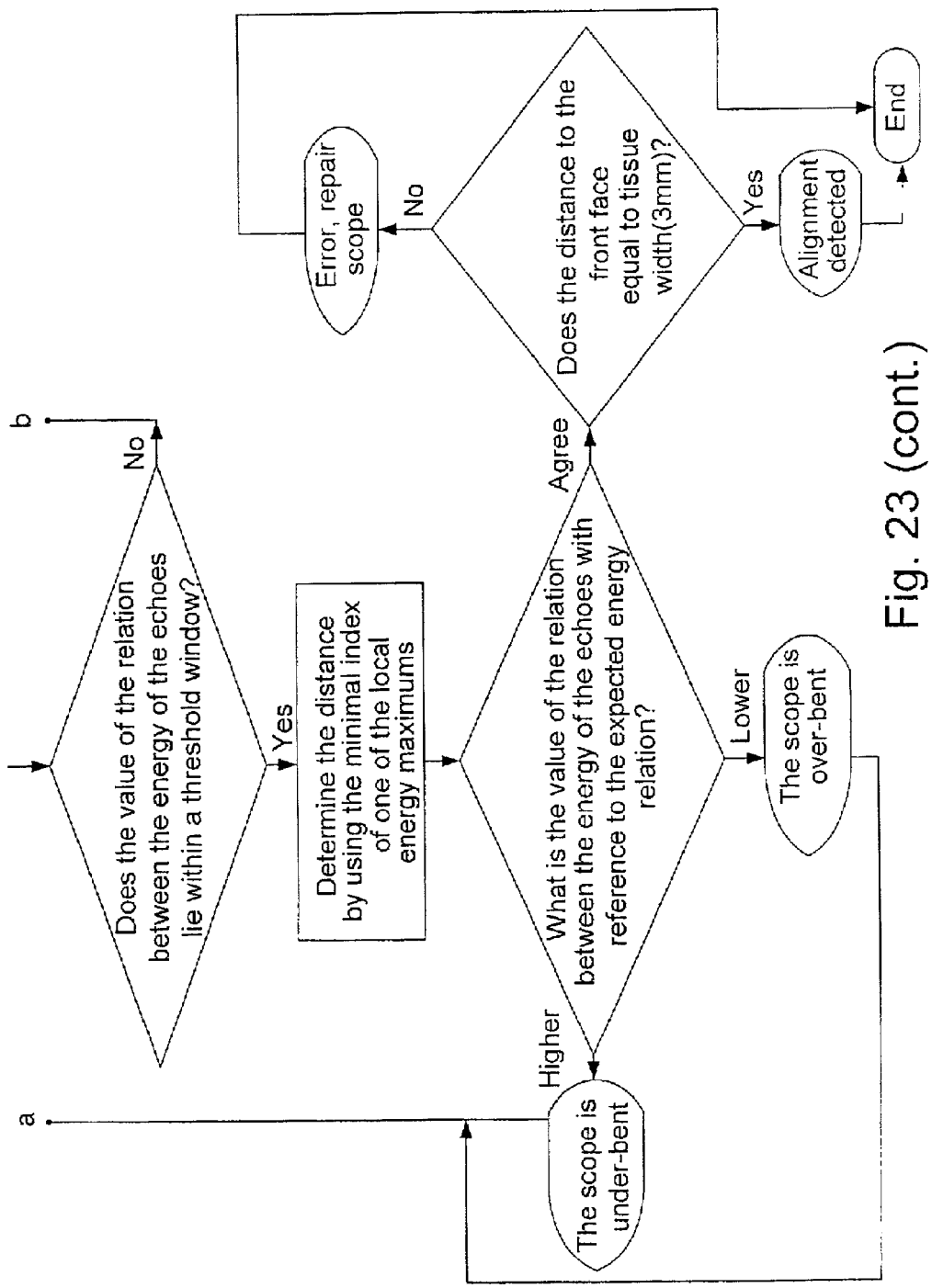

FIG. 23 is a flow chart of the alignment algorithm. The alignment is considered to be correct if, and only if, the echoes are measured at the distance that corresponds to the depth of the step and satisfy the amplitude relations.

In order to reduce the time of calculation, it is possible to find the maxima in the received buffer instead of the correlation maxima. However, in this case, errors occur when random noise with high amplitude occurs. Therefore in a preferred embodiment of the invention the calculation is made using the correlation peaks of the energy (equivalent to the integration of the intensity) and not by using the maxima from the received buffer.

Although embodiments of the invention have been described by way of illustration, it will be understood that the invention may be carried out with many variations, modifications, and adaptations, without departing from its spirit or exceeding the scope of the claims. It should be especially clear to the skilled person, that, although many of the embodiments of the invention have been presented in terms of a stapler incorporated into an endoscope, the invention can easily be applied to the case of other instruments either mounted on the same device or on separate devices used to transport them to the position where they must be brought together to perform a required task. It should be equally clear that, although many of the embodiments of this invention have been described in terms of a specific medical procedure, the invention can be used in a wide variety of medical and industrial applications.

REFERENCES

[1] D. A. Christensen, Ultrasonic Bioinstrumentation, p. 131.

[2] G. S. Kino, Acoustic Waves: Devices, Imaging and Analog Signal Processing. New Jersey: Prentice-Hall Inc., 1987, pp. 175, 220-225.

[3] John G. Proakis and Dimitris G. Manolakis, Digital Signal Processing Principles, Algorithms, and Application, Third Edition, Prentice-Hall International Inc., New Jersey, 1966, pp. 30, 130-131.

[4] William W. Seto, Acoustics, Schaum's Outline Series, McGraw-Hill. Inc., USA, 1971, pp. 13-14.

The invention claimed is:

1. Endoscopic device comprising an articulation section and a system for measuring the distance between and the relative alignment of two objects located at two different locations along the length of said endoscopic device, said system comprising: one or more single ultrasonic transducers, used to both transmit and receive the ultrasonic signals, mounted on, or near, the first object and at least one reflector mounted on, or near, the second object, said reflector being suitable to reflect back a pattern that can be translated into the position and orientation of said objects relative to each other; wherein,
   one of said objects is located on the proximal end or proximally of said articulation section and the other of said objects is located distally of said articulation section.

2. Endoscopic device according to claim 1, wherein the reflector comprises two, or more, parallel reflecting planar surfaces intersected, at an angle of 90 degrees or less, by one or more planes to form one, or more, step-like configurations.

3. Endoscopic device according to claim 2, wherein some or all of the steps in the reflector have different depths and/or different lengths and/or different cross-sections.

4. Endoscopic device according to claim 2, wherein, for the case of reflectors having two or more steps, the total width of the steps does not exceed the beam width of the ultrasonic beam that impinges upon the reflector.

5. Endoscopic device according to claim 2, wherein the distance between reflecting surfaces (step height) is equal or greater than the echo duration multiplied by the sound velocity in the medium divided by two.

6. Endoscopic device to claim 2, wherein the reflecting surfaces of the reflectors are surrounded with ultrasonic energy absorbing material.

7. Endoscopic device according to claim 2, wherein said endoscopic device is adapted to position the two objects within a human or animal body separated by at least one layer of tissue.

8. Endoscopic device according to claim 7, wherein air gaps, which occur between the tissue and the reflecting surfaces of the reflector are filled with a hard or flexible material having an acoustical coefficient matching that of said tissue.

9. Endoscopic device according to claim 7, wherein the air gaps, which occur between the tissue and the reflecting surfaces of the reflector, are filled with medical ultrasonic gel.

10. Endoscopic device according to claim 1, wherein the reflector comprises two, or more, parallel reflecting planar surfaces separated by perpendicular surfaces to form one, or more, step-like configurations with a cylindrical symmetry created by drilling coaxial bores of different diameters.

11. Endoscopic device according to claim 1, wherein two reflectors are mounted at right angles to each other.

12. Endoscopic device according to claim 1, wherein two or more ultrasonic transducers are mounted on, or near, the first object, said transducers being mounted at a predetermined, fixed angle such that the transmitted beams intersect at a point in front of said first object and one ultrasonic reflector is mounted on, or near, the second object which is displaced according to information received from intensity measurements until said reflector is located at said intersection point, thus achieving proper positioning of said objects relative to each other.

13. Endoscopic device according to claim 1, wherein two or more reflectors are mounted on, or near, the first object and one ultrasonic transducer is mounted on, or near, the second object said transducer being composed of an array that produces a beam that can be steered by electronic means in accordance with information received from measurements of the angles to said reflectors until said angles are equal to predetermined values, thereby to achieve proper positioning of said objects relative to each other.

14. Endoscopic device according to claim 1, wherein said endoscopic device comprises an anvil unit of a stapler system, which is one of the objects to be aligned, and a stapler deployment unit containing a stapler cartridge, which is the other object.

15. An endoscopic device according to claim 14, wherein one or more reflectors of ultrasonic waves is created on or within or as an integral part of a surface of the stapler cartridge.

16. An endoscopic device according to claim 14, wherein the transducer is mounted into the stapler anvil unit or the cartridge unit.

17. Endoscopic device according to claim 1, wherein the relative alignment of the two objects is determined by use of triangulation techniques.

18. Endoscopic device according to claim 1, wherein the ultrasonic transducers are single element transducers.

19. Endoscopic device according to claim 1, wherein the ultrasonic transducers are composed of an array of elements.

20. Endoscopic device according to claim 1, wherein an aperture is placed before the transmitting ultrasonic transducers or a diverging transducer is used to cause the transmitted ultrasonic beam to diverge.

21. A method for measuring the distance between two objects located at two different locations along the length of an endoscopic device, said method comprising the steps of:
   a) providing an endoscopic device according to claim 1;
   b) activating the a single ultrasonic transducer used to both transmit and receive the ultrasonic signals to transmit an ultrasonic signal;
   c) activating the single ultrasonic transducer used to both transmit and receive the ultrasonic signals to receive an ultrasonic signal reflected from the reflector;
   d) measuring the time of flight of said signal;
   e) determining the distance between said transducer and said reflector from said measured time; and,
   f) determining the distance between said two objects from the distance between said transducer and said reflector.

22. A method according to claim 21, wherein the time of flight is measured by starting a clock simultaneously with the start of transmission of an ultrasonic signal and stopping said clock when the received signal rises above a predetermined threshold.

23. A method according to claim 21, wherein the time of flight is measured by transmitting an ultrasonic signal, sampling the received signal, and carrying out a cross-correlation with a stored reference signal.

24. A method according to claim 23, comprising transmitting an ultrasonic signal consisting of a random sequence of pulses.

25. A method according to claim 24, comprising modulating the transmitted random sequence of by digital modulation.

26. A method according to claim 25, comprising carrying out the digital modulation by means of the PSK method.

27. A method according to claim 21, comprising using triangulation techniques to determine the relative distance and alignment of the two objects.

28. A method according to claim 27, comprising accomplishing the relative alignment of the two objects in threedimensional space by: providing a single ultrasonic transducer, used to both transmit and receive the ultrasonic signals located on, or near, the first of said objects and three reflectors located on, or near, the second object, measuring the lengths of the sides of the triangles formed by said transducer and each pair of said reflectors, and moving said transducer until a predetermined relationship between said lengths of said sides of said triangles is achieved.

29. A method according to claim 28, comprising replacing the single ultrasonic transducer, used to both transmit and receive the ultrasonic signals and the three reflectors by three ultrasonic transducers, used to both transmit and receive the ultrasonic signals and one reflector.

30. A method according to claim 27, comprising accomplishing the relative alignment of the two objects in two-dimensional space by: providing a single ultrasonic transducer, used to both transmit and receive the ultrasonic signals located on, or near, the first of said objects and two reflectors located on, or near, the second object, measuring the length of the sides of the triangles formed by said transducer and each pair of said reflectors, and moving said transducer until a predetermined relationship between said lengths of said sides of said triangles is achieved.

31. A method according to claim 27, comprising using single element ultrasonic transducers.

32. A method according to claim 27, comprising using ultrasonic transducers comprised of an array of elements.

33. A method according to claim 27, comprising placing an aperture before the transmitting ultrasonic transducer or using a diverging transducer to cause the transmitted ultrasonic beam to diverge.

34. A method according to claim 21, comprising mounting a single ultrasonic transducer, used to both transmit and receive the ultrasonic signals on, or near, the first object and at least one reflector, which reflects back a pattern that can be translated into the position and orientation of said objects relative to each other, on, or near, the second object.

35. A method according to claim 34, wherein the reflector comprises two, or more, parallel reflecting planar surfaces intersected, at an angle of 90 degrees or less, by one or more planes to form one, or more, step-like configurations.

36. A method according to claim 35, wherein some or all of the steps in a two or more step reflector have different depths.

37. A method according to claim 35, wherein, the reflectors have two or more steps and the total width of the steps does not exceed the beam width of the ultrasonic beam that impinges upon the reflector.

38. A method according to claim 35, wherein the distance between reflecting surfaces (step height) is equal or greater than the echo duration multiplied by the sound velocity in the medium divided by two.

39. A method according to claim 35, comprising using the endoscopic device to position the two objects within a human or animal body such that they are separated by at least one layer of tissue.

40. A method according to claim 39, comprising filling the-air gaps, which occur between the tissue and the reflecting surfaces of the reflector with a hard or flexible material having an acoustical coefficient matching that of said tissue.

41. A method according to claim 39, comprising filling the air gaps, which occur between the tissue and the reflecting surfaces of the reflector with medical ultrasonic gel.

42. A method according to claim 34, wherein the reflector comprises two, or more, parallel reflecting planar surfaces separated by perpendicular surfaces to form one, or more, step-like configurations with a cylindrical symmetry created by drilling coaxial bores of different diameters.

43. A method according to claim 34, comprising mounting two reflectors at right angles to each other.

44. A method according to claim 21, comprising surrounding the reflecting surfaces of the reflectors with ultrasonic energy absorbing material.

45. A method according to claim 21, wherein the alignment of the two objects relative to each other is determined by the following steps:
   using a single transducer as a transmitter/receiver of an ultrasonic beam and a reflector having at least one-step, which will give at least two distinct signals in the return beam;
   correlating the signals stored in the computer main memory with those of the predefined reference signal in the computer memory;
   determining the step depths from the buffers corresponding to said maxima of said correlations, wherein, at least two local maxima of the correlation must exist and the difference(s) between them must correspond to the known depth(s) of the step(s);
   if the measured depth(s) of the step(s) do not agree with the known depth(s) of said step(s), then moving the transducer relative to the reflector and carrying out the correlation again; and
   when the measured depth(s) of the step(s) do agree with the known depth(s) of said step(s), then use the results of the correlation to determine the energy relation between said signals in said buffers.

46. A method according to claim 45, comprising using the intensity maxima from the buffer to determine the alignment.

47. A method according to claim 45, comprising using the ratio of the integration of the echoes to determine the alignment.

48. A method according to claim 21, wherein the displacement of the objects relative to each other is determined and changed by the following steps:
   a) using a single transducer as a transmitter/receiver of an ultrasonic beam and a reflector having at least two-steps of different depths, which will give at least three distinct echoes in the return beam;
   b) determining that the objects are not aligned if less than the expected number of echoes is returned;
   c) determining the depth of the steps from the returned echoes;
   d) comparing the measured depth with the known depths of the reflector, to determine the portion of the reflector upon which the ultrasonic beam impinges;
   e) check that the ratio of energy of the two echoes that match the step depth are within a certain relation;
   f) using the information obtained in the steps (d) and (e), to move the transmitter/receiver relative to the reflector; and,
   g) repeating steps (b) to (f) until the transmitter receiver is positioned directly in front of the reflector.

49. A method according to claim 21, wherein the distance between the transducer and the reflector is determined by using a transducer capable of transmitting ultrasonic signals at least two different wavelengths and measuring the ratio of the intensities of the received signals at each wavelength.

50. A method according to claim 21, comprising mounting two or more ultrasonic transducers, on, or near, the first of the objects, at a predetermined, fixed angle such that the transmitted beams intersect at a point in front of said first object and mounting one reflector on, or near, the second object said second object according to information received from intensity measurements until said reflector is located at said intersection point, thus achieving proper positioning of said objects relative to each other.

51. A method according to claim 50, comprising causing the intersection point of the transmitted beams to be located within the Fresnel zone of the ultrasonic transducers.

52. A method according to claim 50, comprising using focused ultrasonic transducers and mounting said ultrasound transducers such that the intersection point of the transmitted beams is located at the focal points of said transducers.

53. A method according to claim 21, comprising mounting two or more ultrasonic reflectors on, or near, the first of the objects and one ultrasonic transducer on, or near, the second object, wherein said transducer is composed of an array that produces a beam that can be steered by electronic means in accordance with information received from measurements of the angles to said receivers and said beam is steered until said angles are equal to predetermined values, thereby to achieve proper positioning of said objects relative to each other.

54. A method according to claim 21, wherein the distance between the transducer and the reflector is measured by the following steps:
  generating a repetitive series of short electrical pulses or bursts of electrical pulses;
  amplifying said pulses;
  applying said amplified electric pulses to a transducer which converts the electrical energy to ultrasonic energy;
  allowing said ultrasonic energy to propagate, in the form of a relatively narrow beam, through a medium, until it encounters a reflector which directs it back towards said transducer from which it was emitted;
  receiving said ultrasonic energy by said transducer which converts it to an electrical signal;
  amplifying and filtering said electrical signal;
  digitizing said signal;
  temporarily storing the sampled data in a separate buffer of a first-in first-out (FIFO) buffer or fast memory;
  transferring the data from the FIFO or fast memory into the main computer memory;
  correlating the data in each buffer with a predefined reference signal pattern stored in a computer memory;
  determining the time of flight of the ultrasonic signal from the index of said buffer where the correlation with said reference signal has its maximum value; and,
  determining the distance from said time of flight.

55. A method according to claim 54, comprising generating the predefined reference signal from a properly chosen mathematical function.

56. A method according to claim 54, comprising measuring an actual received ultrasonic signal and storing it in the computer memory to serve as the predefined reference signal.

* * * * *